US008188335B2

(12) United States Patent
Pereira et al.

(10) Patent No.: US 8,188,335 B2
(45) Date of Patent: May 29, 2012

(54) Δ9-ELONGASE FOR PRODUCTION OF POLYUNSATURATED FATTY ACID-ENRICHED OILS

(75) Inventors: Suzette Pereira, Westerville, OH (US);
Tapas Das, Singapore (SG);
Padmavathy Krishnan, Hilliard, OH (US); Pradip Mukerji, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 211 days.

(21) Appl. No.: 12/505,293

(22) Filed: Jul. 17, 2009

(65) Prior Publication Data
US 2011/0016585 A1 Jan. 20, 2011

(51) Int. Cl.
*A01H 1/00* (2006.01)
*A01H 5/00* (2006.01)
*C12N 5/14* (2006.01)
*C12N 5/16* (2006.01)
*C07H 21/04* (2006.01)

(52) U.S. Cl. ........ 800/278; 800/281; 800/295; 800/297; 800/298; 800/306; 800/312; 800/314; 800/320; 800/320.1; 800/322; 435/410; 435/419; 435/320.1; 435/254.1; 536/23.2; 536/23.7

(58) Field of Classification Search .................. None
See application file for complete search history.

(56) References Cited

U.S. PATENT DOCUMENTS

| | | | |
|---|---|---|---|
| 4,582,788 A | 4/1986 | Erlich |
| 4,666,701 A | 5/1987 | Horrobin et al. |
| 4,683,194 A | 7/1987 | Saiki et al. |
| 4,683,202 A | 7/1987 | Mullis et al. |
| 4,758,592 A | 7/1988 | Horrobin et al. |
| 4,826,877 A | 5/1989 | Stewart et al. |
| 4,943,674 A | 7/1990 | Houck et al. |
| 4,945,050 A | 7/1990 | Sanford et al. |
| 5,004,863 A | 4/1991 | Umbeck et al. |
| 5,106,739 A | 4/1992 | Comai et al. |
| 5,107,065 A | 4/1992 | Shewmaker et al. |
| 5,116,871 A | 5/1992 | Horrobin et al. |
| 5,159,135 A | 10/1992 | Umbeck |
| 5,175,095 A | 12/1992 | Martineau et al. |
| 5,188,958 A | 2/1993 | Moloney et al. |
| 5,231,020 A | 7/1993 | Jorgensen et al. |
| 5,416,011 A | 5/1995 | Hinchee et al. |
| 5,420,034 A | 5/1995 | Kridl et al. |
| 5,443,974 A | 8/1995 | Hitz et al. |
| 5,463,174 A | 10/1995 | Moloney et al. |
| 5,518,908 A | 5/1996 | Corbin et al. |
| 5,552,306 A | 9/1996 | Thomas et al. |
| 5,569,834 A | 10/1996 | Hinchee et al. |
| 5,589,379 A | 12/1996 | Kridl et al. |
| 5,631,152 A | 5/1997 | Fry et al. |
| 5,700,671 A | 12/1997 | Prieto et al. |
| 5,750,176 A | 5/1998 | Prieto et al. |
| 5,912,120 A | 6/1999 | Goldstein et al. |
| 7,645,604 B2 * | 1/2010 | Damude et al. ............... 435/193 |
| 2008/0194685 A1 | 8/2008 | Damude et al. |

FOREIGN PATENT DOCUMENTS

| | | |
|---|---|---|
| EP | 0050424 B1 | 9/1985 |
| EP | 0084796 B1 | 5/1990 |
| EP | 0237362 B1 | 3/1992 |
| EP | 0201184 B1 | 12/1992 |
| EP | 0258017 B1 | 6/1997 |
| WO | 9311245 | 6/1993 |
| WO | 9411516 | 5/1994 |
| WO | 9524494 | 9/1995 |
| WO | 9613591 | 5/1996 |
| WO | 2008124048 A2 | 10/2008 |
| WO | 2008128241 A1 | 10/2008 |
| WO | 2010042510 A1 | 4/2010 |

OTHER PUBLICATIONS

BLAST search results.*
Toriyama, Theor Appl Genet (1986) 73:16-19.
McKently, et al., Plant Cell Rep., 1995, vol. 14, p. 699-703.
International Search Report and Written Opinion for PCT/US2010/041893 dated Oct. 1, 2010.
Singh, et al., "Metabolic engineering of new fatty acids in plants", Current Opinion in Plant Biology, vol. 8, No. 2, Apr. 1, 2005, pp. 197-203.
Napier, "The production of unusual fatty acids in transgenic plants", Annual Review of Plant Physiology and Plant Molecular Biology, vol. 58, Jan. 1, 2007, pp. 295-319.
Lassner, et al., The Plant Cell, 1996, vol. 8, p. 281-292.
Smith & Waterman, Adv. Appl. Math., 1981, vol. 2, p. 482-489.
Needleman & Wunsch, J. Mol. Biol., 1970, vol. 48, p. 443-453.
Pearson & Lipman, Proc. Natl. Acad. Sci. (USA), 1988, vol. 85, p. 2444-2448.
Higgins, et al., CABIOS, 1989, 5L 151-153.
Altschul, et al., Nucleic Acids Research, 1997, vol. 25, p. 3389-3402.
Ingelbrecht, et al., Plant Cell, 1989, vol. 1, p. 671-680.
Mullis, et al., Cold Spring Harbor Symp. Quant. Biol., 1986, vol. 51, p. 263-273.
Okamuro & Goldberg, Biochemistry of Plants, 1989, vol. 15, p. 1-82.
Jones, et al., EMBO J., 1985, vol. 4, p. 2411-2418.
Almeida, et al., Mol. Gen. Genetics, 1989, vol. 218, p. 78-86.
Klein, et al., Nature (London), 1987, vol. 327, p. 70-73.
Ishida, et al., Nature, 1996, vol. 14, p. 745-750.
Turner & Foster, Molecular Biotechnology, 1995, vol. 3, p. 225-236.
Schnieke, et al., Science, 1997, vol. 278, p. 2130-2133.
McCabe, et al., Bio/Technology, 1988, vol. 6, p. 923-926.
Christou, et al., Plant Physiol., 1988, vol. 87, p. 671-674.
Cheng, et al., Plant Cell Rep., 1996, vol. 15, p. 653-657.
Janeiro, et al., Plant Cell Rep., 1996, vol. 15, p. 699-703.
Grant, et al., Plant Cell Rep., 1995, vol. 15, p. 254-258.
Bytebier, et al., Proc. Natl. Acad. Sci. (USA), 1987, vol. 84, p. 5345-5349.

(Continued)

Primary Examiner — Eileen B O Hara

(57) ABSTRACT

The present disclosure relates to isolated polynucleotides encoding a delta 9-elongase, delta 9-elongases encoded by the isolated polynucleotides, expression vectors comprising the isolated polynucleotides, host cells comprising the expression vectors, and methods for producing delta 9-elongase and polyunsaturated fatty acids.

33 Claims, 22 Drawing Sheets

OTHER PUBLICATIONS

Wan and Lemaux, Plant Physiol., 1994, vol. 104, p. 37-48.
Rhodes, et al., Science, 1988, vol. 240, p. 204-207.
Gordon-Kamm, et al., Plant Cell, 1990, vol. 2, p. 603-618.
Fromm, et al., Bio/Technology, 1990, vol. 8, p. 833-839.
Koziel, et al., Bio/Technology, 1993, vol. 11, p. 194-200.
Armstrong, et al., Crop Science, 1995, vol. 35, p. 550-557.
Somers, et al., Bio/Technology, 1992, vol. 10, p. 15-89.
Horn, et al., Plant Cell Rep., 1988, vol. 7, p. 469-472.
Toriyama, et al., Theor. Appl. Genet., 1986, vol. 205, p. 34.
Park, et al., Plant Mol. Biol., 1996, vol. 32, p. 1135-1148.
Abedinia, et al., Aust. J. Plant Physiol., 1997, vol. 24, p. 133-141.
Zhang and Wu, Theor. Appl. Genet., 1988, vol. 76, p. 835-840.
Zhang, et al., Plant Cell Rep., 1988, vol. 7, p. 379-384.
Battraw and Hall, Plant Sci., 1992, vol. 86, p. 191-202.
Christou, et al., Bio/Technology, 1991, vol. 9, p. 957-962.
De la Pena, et al., Nature, 1987, vol. 325, p. 274.
Bower and Birch, Plant J., 1992, vol. 2, p. 409-416.
Wang, et al., Bio/Technology, 1992, vol. 10, p. 691-696.
Vasil, et al., Bio/Technology, 1992, vol. 10, p. 667-674.
Marcotte, et al., Nature, 1988, vol. 335, p. 454-457.
McCarty, et al., Plant Cell, 1989, vol. 1, p. 523-532.
McCarty, et al., Cell, 1991, vol. 66, p. 895-905.
Hattori, et al., Genes Dev., 1992, vol. 6, p. 609-618.
Goff, et al., EMBO J., 1990, vol. 9, p. 2517-2522.
Horrobin, et al., Am. J. Clin. Nutr., 1993, vol. 57 (Suppl.), p. 732S-737S.
Brenner, et al., Adv. Exp. Med. Biol., 1976, vol. 83, p. 85-101.
Leonard, et al., Prog Lipid Res., 2004, vol. 43, p. 36-54.
Nielsen, et al., Plant Cell, 1989, vol. 1, p. 313-328.
Clough, et al., Plant J., 1998, vol. 16, p. 735-743.
Cahoon, et al., Phytochemistry. 2006. vol. 67, p. 1166-1176.
Pidkowich, et al., Proc. Natl. Acad. Sci. (USA), 2007, vol. 104, p. 4742-4747.
Cahoon and Shanklin, Proc. Natl. Acad. Sci. (USA), 2000, vol. 97, p. 12350-12355.

* cited by examiner

```
Eug-MO7-ELO #10(451) CTGCAGTACGAAAACGAGGCCCTGTGTCTTCCTCGATCTTTCGTCTTCCTCAACGGCTT 500
Eug-MO7-ELO #14(451) CTGCAGTACGAAAACGAGGCCCTGTGTCTTCGTCGATCTTTCGTCTTCCTCAACGGCTT 550

Eug-MO7-ELO #10(501) CATCCACTTCATCATGTATACTACTGGGCCCGGCCCGGGTGAAGCTCC 550
Eug-MO7-ELO #14(501) CATCCACTTCATCATGTATACTACTGGGCCCGGCCCGGGTGAAGCTCC 600

Eug-MO7-ELO #10(551) CGTTCCCCGTGCCCGAAGTCGTTCACCTCCATGCAGATCATCCAGTTC 600
Eug-MO7-ELO #14(551) CGTTCCCCGTGCCCGAAGTCGTTCACCTCCATGCAGATCATCCAGTTC 650

Eug-MO7-ELO #10(601) AACCTGGCTTCTACTCGTGTGGCGTACCACACG ATCCGTGCTACCG 650
Eug-MO7-ELO #14(601) AACCTGGCTTCTACTCGTGTGGCGTACCACACA ATCCGTGCTACCG 700

Eug-MO7-ELO #10(651) ACAGGACCCAATGCGAATGTTCGCCTCTTCAACTACTTCTACGTGG 700
Eug-MO7-ELO #14(651) ACAGGACCCAATGCGAATGTTCGCCTCTTCAACTACTTCTACGTGG 750

Eug-MO7-ELO #10(701) GAGTGGTCTTACTCGTGTTTTGAATTTCTACGTGCACGTAGTGATC 750
Eug-MO7-ELO #14(701) CAGTGGTCTTACTCGTGTTTTGAATTTCTACGTGCACGTAGTGATC 800

Eug-MO7-ELO #10(751) AAGAA GCGGCGGCTGGCCGAAGATCAGAAGAAAGTGGACTAGAAGCT 800
Eug-MO7-ELO #14(751) AAGAG GCGGCGGCTGGCCGAAGATCAGAAGAAAGTGGACTAGAAGCT

Eug-MO7-ELO #10(801) T
Eug-MO7-ELO #14(801) T
```

FIG. 3A

```
                     1                                                        50
Eug-MO7-ELO-10  (1)  ---------------MDVATTLAGIAADVLPRVDYARLGRDAAACEVLY
E. gracialis-D9 (1)  ---------------MEVVNEIVSIGQEVLPKVDYAQLWSDASHCEVLY
I. galbana-D9   (1)  ---------------------MALANDAGERIWAAVTDPEILI
Mouse-Elov14    (1)  MGLLDSEPGSVLNAMSTAFNDTVEFYRWTWTIADKRVADWPLMQSPWPTI
human-ELOVL2    (1)  ---------------MEHLKAFDDEINAFLDNMFGPRDSRVRGWFMLDSYLPTF
C. elegans-ELO  (1)  ---MAQHPLVQRLLDVKFDTKRFVAIATHGPKNFPDAEGRKFFADHFDVTI 51                                                       100
Eug-MO7-ELO-10  (35) LSLFFIAMKFILRPLG--DKGQARLKSLFTLYNLVMSIYSLGSFVVMGYA
E. gracialis-D9 (35) LSIAFVILKFTLGPLG--PKGQSRMKFVFTNYNLLMSIYSLGSFLSMAYA
I. galbana-D9   (23) GTFSYLLLKPLLRNSGLVDEKKGAYRTSMIWYNVLLALFSALSFYVTATA
Mouse-Elov14    (51) SISTLYLFVWLGPKWMKDREPFQMRLVLIIYNFGMVLLNLFIFRELFMG
human-ELOVL2    (40) FLTVMYLLSIWLGNKYMKNRPALSLRGILTLYNLGITLLSAYMLAELILS
C. elegans-ELO  (49) QASILYMVVVFGTKWFMRNRQPFQLTIPLNIWNFILAAFSIAGAVKMTPE 101                                                      150
Eug-MO7-ELO-10  (83) LA----------DIGVLGGDCGKAFSNPMFRLTAQLFYISKIYVEY
E. gracialis-D9 (83) MY----------TIGVMSDNCEKAFDNNVFRITTQLFYLSKIFLEY
I. galbana-D9   (73) LGWDYGTGAWLRRQTGDTPQPLFQCPSPVWDSKLFTWTAKAFYYSKIYVEY
Mouse-Elov14   (101) SY--------N-AGYSYICQSVDYSNDVNEVRIAAALWWYFVSKIGVEY
human-ELOVL2    (90) TW--------E--GGYNLQCQDLTSAGEADIRVAKVLWWYFSKISVEF
C. elegans-ELO  (99) FF----------GTIANKGIVASYCKVFDFTKGENGYWWLFMASKLFEL 151                                                      200
Eug-MO7-ELO-10 (118) IDSFYVLQTNK--PLTYLQFFHHLGAPVDLWLFLQYENEALWIF-VFLNG
E. gracialis-D9(118) IDSFYLPLMGK--PLTWQFFHHLGAPMDMWLFYNYRNEAVWIF-VLLNG
I. galbana-D9  (123) LDTAWLVLKGK--RVSFLQAFHHFGAPWDVYLGIRLHNEGVWIF-MFFNS
Mouse-Elov14   (140) LDTVFFIQRKKNNQVSFLHVYHHCTMFTLWWIGIKWVAGGQAFFGAQMNS
human-ELOVL2   (128) LDTIFFVLRKKTSQITFLHVYHHASMFNIWWCVLNWIPCGQSFFGPTLNS
C. elegans-ELO (139) VDTIFLVLRKR--PLMFLHWYHHILTMIYAWYSHPLTPGFNRYG-IYLNF
```

FIG. 3B

```
                    201                                                                250
Eug-MO7-ELO-10 (165) FIHFIMYGYYWARLVKLPFPVP---KSFITSMQIIQFNLG--FYLVWRYH
E. gracialis-D9 (165) FIHWIMYGYYWTRLIKLKFPMP---KSLITSMQIIQFNVG--FYIVWKYR
I. galbana-D9   (170) FIHTIMYTYYGLTAAGYKFKA----KPLITAMQICQFVGG--FLLVWDYI
Mouse-Elov14    (190) FIHVIMYSYYGLTAFGPWIQKYLWWKRYLTMLQLVQF-----H-VTIGHT
human-ELOVL2    (178) FIHILMYSYYGLSVFPSMHKYL-WWKKYLTQAQLVQFV----LTITHT
C. elegans-ELO  (186) VVHAFMYSYYFLRSMKIRVPGF--IAQAITSLQIVQFIISCAVLAHLGYL 251                                                                300
Eug-MO7-ELO-10 (210) TIPCYRQDPMRMFAWLFNYFYVGVLLLFLNFYVHTYVIKKARRLAKDEK
E. gracialis-D9 (210) NIPCYRQDGMRMFGWFFNYFYVGTVLCLFLNFYVQTYIVRKHKGAKKIQ-
I. galbana-D9   (214) NVPCFNSDKGKLFSWAFNYAYVGSVFLLFCHFFYQDNLATKKSAKAGKQL
Mouse-Elov14    (234) ALSLYTDCPFPKWMHWALIAYAISFIFLFLNFYTRTYNEPKQSKTGKTAT
human-ELOVL2    (221) MSAVVKPCGFPFGCLIFQSSYMLTLVILFLNFYVQTYRKKPMKKDMQEPP
C. elegans-ELO  (234) MHFTNANCDFEPSVFKLAVFMDTTYLALFVNFFLQSYVLRGGKDKYKAVP 301                  329
Eug-MO7-ELO-10 (260) KVD-----------------------------------------------
E. gracialis-D9 (259) --------------------------------------------------
I. galbana-D9   (264) --------------------------------------------------
Mouse-Elov14    (284) NGISSNGVNKSEKALENGKPQKNGKPKGE
human-ELOVL2    (271) AGKEVKNGFSKAYFTAANGVMNKKAQ---
C. elegans-ELO  (284) KKKNN--------------------------
```

FIG. 4A

*Pavlova salina* Δ9-elongase (SEQ ID NO: 1)

```
  1 MKAAAGKVQQEAERLTAGLWLPMMLAAGYLLVLSANRASFYENINNEKGA
 51 YSTSWFSLPCVMTAVYLGGVFGLTKYFEGRKPMQGLKDYMFTYNLYQVII
101 NVWCIAAFVVEVRRAGMSAVGNKVDLGPNSFRLGFVTWVHYNNKYVELLD
151 TLWMVLRKKTQQVSFLHVYHHVLLIWAWFCVVKFCNGGDAYFGGMLNSII
201 HVMMYSYYTMALLGWSCPWKRYLTQAQLVQFCICLAHATWAAATGVYPFH
251 ICLVEIWMVSMLYLFTKFYNSAYKGAAKGAASSNGAAAPSGAKPKSIK
301 AN
```

FIG. 4B

*Isochrysis galbana* Δ9-elongase (SEQ ID NO: 2)

```
  1 MALANDAGERIWAAVTDPEILIGTFSYLLLKPLLRNSGLVDEKKGAYRTS
 51 MIWYNVLLALFSALSFYVTATALGWDYGTGAWLRRQTGDTPQPLFQCPSP
101 VWDSKLFTWTAKAFYYSKYVEYLDTAWLVLKGKRVSFLQAFHHFGAPWDV
151 YLGIRLHNEGVWIFMFFNSFIHTIMYTYYGLTAAGYKFKAKPLITAMQIC
201 QFVGGFLLVWDYINVPCFNSDKGKLFSWAFNYAYVGSVFLLFCHFFYQDN
251 LATKKSAKAGKQL
```

FIG. 4C

*Eutreptiella sp.* Δ9-elongase (SEQ ID NO: 3)

```
  1 MAAVIEVANEFAAITAETLPKVDYQRLWRDIYSCELLYFSIAFVILKFTL
 51 GELSDSGKKILRVLFKWYNLFMSVFSLVSFLCMGYAIYTVGLYSNECDRA
101 FDNSLFRFATKVFYSKFLEYIDSFYLPLMAKPLSFLQFFHHLGAPMDMW
151 LFVQYSGESIWIFVFLNGFIHFVMYGYYWTRLMKFNFPMPKQLITAMQIT
201 QFNVGFYLVWWYKDIPCYRKDPMRMLAWIFNYWYVGTVLLFINFFVKSY
251 VFPKPKTADKKVQ
```

FIG. 4D

*Euglena gracialis* Δ9-elongase (SEQ ID NO:4)

```
  1 MEVVNEIVSIGQEVLPKVDYAQLWSDASHCEVLYLSIAFVILKFTLGPLG
 51 PKGQSRMKFVFTNYNLLMSIYSLGSFLSMAYAMYTIGVMSDNCEKAFDNN
101 VFRITTQLFYLSKFLEYIDSFYLPLMGKPLTWLQFFHHLGAPMDMWLFYN
151 YRNEAVWIFVLLNGFIHWIMYGYYWTRLIKLKFPMPKSLITSMQIIQFNV
201 GFYIVWKYRNIPCYRQDGMRMFGWFFNYFYVGTVLCLFLNFYVQTYIVRK
251 HKGAKKIQ
```

FIG. 4E

*Euglena anabaena* Δ9-elongase (SEQ ID NO: 5)

```
  1 MEAAKELVSIVQEELPKVDYAQLWQDASSCEVLYLSVAFVAIKFMLRPLD
 51 LKRQATLKKLFTAYNFLMSIYSFGSFLAMAYALSVTGILSGDCETAFNND
101 VFRITTQLFYLSKFVEYIDSFYLPLMDKPLSFLQFFHHLGAPIDMWLFYK
151 YRNEGVWIFVLLNGFIHWIMYGYYWTRLIKLNFPMPKNLITSMQIIQFNV
201 GFYIVWKYRNVPCYRQDGMRMFAWIFNYWYVGTVLLLFLNFVQTYIRKP
251 RKNQGKKE
```

FIG. 5A

SEQ ID NO: 6

```
  1 TTTCGGTCCGGATTCCCGGGAATTTTTTTCGTGTTGCCTGGCTAGTACG
 51 CCCCCTCCTCCTGTGACCCTCCACCACACCCCCAAAGGATGGACG
101 TCGCGACTACGCTGGCTGGCATCGCGGACGTGCTGCCCGCGTGGAC
151 TACGCGCGGGCTTGGGCGCGACGCCGCGCTGCGAGGTTCTATACCTTTC
201 GCTGTTCTTCATCGCCATGAAGTTCATCCTTCGCCCCTCGGCGACAAGG
251 GGCAGGCCCGCCTCAAGTCGCTCTCTTCACCCTCTACAACCTCGTGATGTCC
301 ATCTACTCCCTCCGGATCTTTCGTTGTAATGGGCTACGCCTTGGCGGATAT
351 CGGAGTGCTGCGGTGTGATTGCGGGAAAGCATTCTCAAATCCCATGTTCC
401 GCCTCACCGCTCAGTTGTTCTACATCAGCAAGTACGTTGAGTACATCGAT
451 TCCTTTCTAGTGCTTCTCCACCAACAAGCCCCTGACCTACCTGCAGTTCTT
501 CCACCACCTCGGAGCCCCGTCGACCTCTGGCTCTTCCTGCAGTACGAAA
551 ACGAGGCGCTGTGGATCTTCGTCTTCCTCAACGGCTTCATCCACTTCATC
601 ATGTACGGGTACTACTGGGCCCGGTGAAGCTCCCGTTCCCCGTGCC
651 GAAGTCGTTCATCACCTCCATGCAGATCATCCAGTTCAACCTGGCTTCT
701 ACCTCGTGTGGCGGTACCACACAATCCGTGCTACGGACAGGAC
```

FIG. 5B

SEQ ID NO: 7

1   MDVATTLAGIAADVLPRVDYARLGRDAAACEVLYLSLFFIAMKFILRPLG
51  DKGQARLKSLFTLYNLVMSIYSLGSFVVMGYALADIGVLGGDCGKAFSNP
101 MFRLTAQLFYISKYVEYIDSFYVLLTNKPLTYLQFFHHLGAPVDLWLFLQ
151 YENEALWIFVFLNGFIHFIMYGYYWARLVKLPFPVPKSFITSMQIIQFNL
201 GFYLVWRYHTIPCYRQD

FIG. 6A

SEQ ID NO: 13

```
  1 TCCCCGTGCCGAAGTCGTTCATCACCTCCATGCAGATCATCCAGTTCAAC
 51 CTGGGCTTCTACCTCGTGTGGCCGTACCACACTATCCGTGTACCGACA
101 GGACCCAATGCGAATGTTCGCTTGGCTCTTCAACTACTTCTACGTGGGAG
151 TGGTCTTACTGCTGTTTTGAATTTCTACACGTGCACACGTACGTGATC
201 AAGAAGGGGCGGGCTGGGCGGAAGGATGAGAGAAGTGGACTAGCGGAG
251 CCGGCGGCGCCCACTGGGACCCGGTGGCTCCGTGCCCTTCCTCGCCCG
301 GCATCGAACCCACCAYTCCCCACTAGCCTCCACGATACTCCCTTCCCT
351 CCTCCCCAGTCCACCGTGAAAGGTATCCAGGCCCTTCGACTCACACTTG
401 CGACCAGATGGCGGGTTTAACCTCTGCGCGACTCGGAGAGTTGCCCTAACC
451 ATCTGTTCTAGAACTCGCGATTGGACTGTGTTGAACTGGATCCGATGACC
501 CTCGTTTTTCCATACCGTTGTWMAAAAAAAAAAAAAAAAAAAAAAAAA
551 A
```

FIG. 6B

1 PVPKSFITSMQIIQFNLGFYLVWRYHTIPCYRQDPMRMFAWLFNYFYVGV
51 VLLFLNFYVHTYVIKKARRLAKDEKKVD*RSRRRPLGPGGSVRPSSPGIE
101 PTHSPTSLHDTPFPPPQSTVERYPGPSTHTCDQMAV*PLRDSESCPNHLF*N
151 SRLDCVELDPMTLVFPYRCXKKKKKKKK

FIG. 6C

SEQ ID NO: 14
1 PVPKSFITSMQIIQFNLGFYLVWRYHTIPCYRQDPMRMFAWLFNYFYVGV
51 VLLFLNFYVHTVIKKARRLAKDEKKVD

FIG. 6D

SEQ ID NO: 30

1 RSRRRPLGPGGSVRPSSPGIEPTHSPTSLHDTPFPPPQSTVERYPGPSTH
51 TCDQMAV

FIG. 6E

SEQ ID NO: 31

1 PLRDSESCPNHLF

FIG. 6F

SEQ ID NO: 32

1 NSRLDCVELDPMTLVFPYRCXKKKKKKKK

FIG. 7A

SEQ ID NO: 17

```
  1  ATGGACGTCGGACTACGCTGGCTGGCATGCGGGCGGACGTGCTGCCCCG
 51  CGTGGACTACGCGGGGCTTGGGCGGCAGCGCGCCTGCGGAGGTTCTAT
101  ACCTTTCGCTGTTCTTCATCGCCATGAAGTTCATCTTCGCCCCCTCGGC
151  GACAAGGGGCAGGCCCGCCTCAAGTCGCTCTTCACCCTCTACAACCTCGT
201  GATGTCCATCTACTCCCTCGGATCTTTCGTTGTAATGGGCTACGCCTTGG
251  CGGATATCGGAGTGCTCGGTGATTGCGGGAAAGCATTCTCAAATCCC
301  ATGTTCCGCCTCACCGCTCAGTTGTTCTACATCAGCAAGTACGTTGAGTA
351  CATCGATTCCTTCTACGTGCTTCTCCACCAACAAGCCCCTGACCTACCTGC
401  AGTTCTTCCACCACCTCGGAGCCGTGGATCTTCGTCTTCCTCAAGGTTCATCCA
451  TACGAAACGAGGCGGTGTACTACTGGGCCCGGCTGGTGAAGCTCCCGTTCC
501  CTTCATCATGTACGGGTACTACTCACCTCCAGATCATCCAGTTCAACCTG
551  CCGTGCCGAAGTCGTTCATCGGGCGGTACCACATCCCGTCTACCGACAGGA
601  GGCTTCTACCTCGTGGCGGAATGTCGCTTGGCTCTTCAACTTCTACGTGGGAGTGG
651  CCCAATGCGAATGCCGAATGCCTCTTCAACTTCTACGTGCACACGTACGTGATCAAGAAA
701  TCTTACTGCTGTTTTTGAATTTCTACGTGCACACGTACGTGATCAAGAAA
751  GCGGGGCTGGCAGGATGAGAAGAAGTGGACTAG
```

FIG. 7B

SEQ ID NO: 18

```
  1 MDVATTLAGIAADVLPRVDYARLGRDAAACEVLYLSLFFIAMKFILRPLG
 51 DKGQARLKSLFTLYNLVMSIYSLGSFVVMGYALADIGVLGGDCGKAFSNP
101 MFRLTAQLFYISKYVEYIDSFYVLLTNKPLTYLQFFHHLGAPVDLWLFLQ
151 YENEALWIFVFLNGFIHFIMYGYYWARLVKLPFPVPKSFITSMQIIQFNL
201 GFYLVWRYHTIPCYRQDPMRMFAWLFNYFYVGVVLLLFLNFYVHTYVIKK
251 ARRLAKDEKKVD*
```

FIG. 8A

SEQ ID NO: 19

```
  1  ATGGACGTCGCGACTACGCTGGCCGGCATCGCGGGCGGACGTGCTGCCCCG
 51  CGTGGACTACGCCGCGGCTTGGGCGCGACGCCGTCGCCTGCGCGAGGTTCTAT
101  ACCTTTCGCTGTTCTTCATCGCCATGAAGTTCATCCTTCGCCCCCTCGGC
151  GACAAGGGGCAGGCCCGCCTCAAGTCGGCTCTTCACCCTCTACAACCTCGT
201  GATGTCCATCTACTCCCTCGGATCTTTCGTTATAATGGGTACGCCTTGG
251  CGGATATCGGAGTGCTCGGTGGTGATTGCGGGAAAGCATTCTCAAATCCC
301  TTGTTCCGCATCACCGCTCAGTTGTTCTACATCAGCAAGTACGTTGAGTA
351  CATCGATTCCTTCTACGTGCTTCTCCACCAACAAGCCCCTGACCTACCTGC
401  AGTTCTTCCACCACCTCGGAGCCCGTGACCTCGGCTTCGTCTTCCTGCAG
451  TACGAAAACGAGGCGCTGGATCTTCGTCTTCCTCAACGGCTTCATCCA
501  CTTCATCATGTACGGGTACTACTCCATCCAGATCATCCAGTTCAACCTG
551  CCGTGCCGAAGTCGTTCGCTTGGCGGTACCACTATCCCGTGCTACCGACAGGA
601  GGCTTCTACCTCGTGTGGCCGTACCACTATCCCGTGCTACCGACAGGA
651  CCCAATGCGAATGTTCGCTTGGCTCTTCAACTTCTACGTGGGAGTGG
701  TCTTACTGCTGTTTTGAATTTCTACGTGCACACGTACGTGATCAAGAAG
751  GCGGGCGGGCTGGCCAAGGATGAGAAGAAAGTGGACTAG
```

FIG. 8B

SEQ ID NO: 20

```
  1 MDVATTLAGIAADVLPRVDYARLGRDAVACEVLYLSLFFIAMKFILRPLG
 51 DKGQARLKSLFTLYNLVMSIYSLGSFVIMGYALADIGVLGGDCGKAFSNP
101 LFRITAQLFYISKYVEYIDSFYVLLTNKPLTYLQFFHHLGAPVDLWLFLQ
151 YENEALWIFVFLNGFIHFIMYGYYWARLVKLPFPVPKSFITSMQIIQFNL
201 GFYLVWRYHTIPCYRQDPMRMFAWLFNYFYVGVLLLFLNFYVHTYVIKK
251 ARRLAKDEKKVD*
```

FIG. 9A

Mouse Elovl4 elongase (SEQ ID NO: 21)

```
  1 MGLLDSEPGSVLNAMSTAFNDTVEFYRWTWTTIADKRVADWPLMQSPWPTI
 51 SISTLYLLFVWLGPKWMKDREPFQMRLVLIIYNFGMVLLNLFIFRELFMG
101 SYNAGYSYICQSVDYSNDVNEVRIAAALWWYFVSKGVEYLDTVFFILRKK
151 NNQVSFLHVYHHCTMFTLWWIGIKWVAGGQAFFGAQMNSFIHVIMYSYYG
201 LTAFGPWIQKYLWWKRYLTMLQLVQFHVTIGHTALSLYTDCPFPKWMHWA
251 LIAYAISFIFLFLNFYTRTYNEPKQSKTGKTATNGISSNGVNKSEKALEN
301 GKPQKNGKPKGE*
```

FIG. 9B

Human ELOVL2 elongase (SEQ ID NO: 22)

1 MEHLKAFDDEINAFLDNMFGPRDSRVRGWFMLDSYLPTFFLTVMYLLSIW
51 LGNKYMKNRPALSLRGILTLYNLGITLLSAYMLAELILSTWEGGYNLQCQ
101 DLTSAGEADIRVAKVLMWYYFSKSVEFLDTIFFVLRKKTSQITFLHVYHH
151 ASMFNIWWCVLNWIPCGQSFFGPTLNSFIHILMYSYYGLSVFPSMHKYLW
201 WKKYLTQAQLVQFVLTITHTMSAVVKPCGFPFGCLIFQSSYMLTLVILFL
251 NFYVQTYRKKPMKKDMQEPPAGKEVKNGFSKAYFTAANGVMNKKAQ*

FIG. 9C

C. elegans elongase (SEQ ID NO: 23)

1   MAQHPLVQRLLDVKFDTKRFVAIATHGPKNFPDAEGRKFFADHFDVTIQA
51  SILYMVVFGTKWFMRNRQPFQLTIPLNIWNFILAAFSIAGAVKMTPEFF
101 GTIANKGIVASYCKVFDFTKGENGYWVLFMASKLFELVDTIFLVLRKRP
151 LMFLHWYHHILTMIYAWYSHPLTPGFNRYGIYLNFVVHAFMYSYYFLRSM
201 KIRVPGFIAQAITSLQIVQFIISCAVLAHLGYLMHFTNANCDFEPSVFKL
251 AVFMDTTYLALFVNFFLQSYVLRGGKDKYKAVPKKKKNN*

Δ9-ELONGASE FOR PRODUCTION OF POLYUNSATURATED FATTY ACID-ENRICHED OILS

BACKGROUND OF THE DISCLOSURE

The present disclosure relates to isolated polynucleotides encoding a delta-9 elongase, delta-9 elongases encoded by the isolated polynucleotides, expression vectors comprising the isolated polynucleotides, host cells comprising the expression vectors, and methods for producing delta-9 elongases and polyunsaturated fatty acids.

Polyunsaturated fatty acids (PUFAs) play many roles in the proper functioning of life forms. For example, PUFAs are important components of the plasma membrane of a cell, where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to efficiently produce them, as well as intermediates leading to their production.

A number of enzymes, most notably desaturases and elongases, are involved in PUFA biosynthesis (see FIG. 1). Desaturases catalyze the introduction of unsaturations (e.g., double bonds) between carbon atoms within the fatty acid alkyl chain of the substrate. Elongases catalyze the addition of a 2-carbon unit to a fatty acid substrate. For example, linoleic acid (LA, 18:2n-6) is produced from oleic acid (OA, 18:1n-9) by a Δ12-desaturase. Eicosadienoic acid (EDA, 20:2n-6) is produced from linoleic acid (LA, 18:2n-6) by a Δ9-elongase. Dihomo-γ-linolenic acid (DGLA, 20:3n-6) is produced from eicosadienoic acid (EDA, 20:2n-6) by a Δ8-desaturase. Arachidonic acid (ARA, 20:4n-6) is produced from dihomo-γ-linolenic acid (DGLA, 20:3n-6) by a Δ5-desaturase (see FIG. 1).

Elongases catalyze the conversion of γ-linolenic acid (GLA, 18:3n-6) to dihomo-γ-linolenic acid (DGLA, 20:3n-6) and the conversion of stearidonic acid (SDA, 18:4n-3) to eicosatetraenoic acid (ETA, 20:4n-3). Elongase also catalyzes the conversion of arachidonic acid (ARA, 20:4n-6) to adrenic acid (ADA, 22:4n-6) and the conversion of eicosapentaenoic acid (EPA, 20:5n-3) to ω3-docosapentaenoic acid (22:5n-3). Δ9-elongase elongates polyunsaturated fatty acids containing unsaturation at the carbon 9 position. For example, Δ9-elongase catalyzes the conversion of linoleic acid (LA, 18:2n-6) to eicosadienoic acid (EDA, 20:2n-6), and the conversion of α-linolenic acid (ALA, 18:3n-3) to eicosatrienoic acid (ETrA, 20:3n-3). ω3-ETrA may then be converted to ω3-ETA by a Δ8-desaturase. ω3-ETA may then be utilized in the production of other polyunsaturated fatty acids, such as ω3-EPA, which may be added to pharmaceutical compositions, nutritional compositions, animal feeds, as well as other products such as cosmetics.

The elongases which have been identified in the past differ in terms of the substrates upon which they act. Furthermore, they are present in both animals and plants. Those found in mammals have the ability to act on saturated, monounsaturated and polyunsaturated fatty acids. In contrast, those found in plants are specific for saturated or monounsaturated fatty acids. Thus, in order to generate polyunsaturated fatty acids in plants, there is a need for a PUFA-specific elongase.

In both plants and animals, the elongation process is believed to be the result of a four-step mechanism (Lassner et al., *The Plant Cell* 8:281-292 (1996)). CoA is the acyl carrier. Step one involves condensation of malonyl-CoA with a long-chain acyl-CoA to yield carbon dioxide and a β-ketoacyl-CoA in which the acyl moiety has been elongated by two carbon atoms. Subsequent reactions include reduction to β-hydroxyacyl-CoA, dehydration to an enoyl-CoA, and a second reduction to yield the elongated acyl-CoA. The initial condensation reaction is not only the substrate-specific step but also the rate-limiting step.

It should be noted that animals cannot desaturate beyond the 49 position, and therefore cannot convert oleic acid (OA, 18:1n-9) into linoleic acid (LA, 18:211-6). Likewise, α-linolenic acid (ALA, 18:311-3) cannot be synthesized by mammals, since they lack Δ15-desaturase activity. However, α-linolenic acid can be converted to stearidonic acid (SDA, 18:4n-3) by a Δ6-desaturase (see WO 96/13591; see also U.S. Pat. No. 5,552,306), followed by elongation to eicosatetraenoic acid (ETA, 20:4n-3) in mammals and algae. This polyunsaturated fatty acid (i.e., ETA, 20:4n-3) can then be converted to eicosapentaenoic acid (EPA, 20:5-3) by a Δ5-desaturase. Other eukaryotes, including fungi and plants, have enzymes which desaturate at carbons 12 (see WO 94/11516 and U.S. Pat. No. 5,443,974) and 15 (see WO 93/11245). The major polyunsaturated fatty acids of animals therefore are either derived from diet and/or from desaturation and elongation of linoleic acid or α-linolenic acid. In view of the inability of mammals to produce these essential long-chain fatty acids, it is of significant interest to isolate genes involved in PUFA biosynthesis from species that naturally produce these fatty acids and to express these genes in a microbial, plant or animal system which can be altered to provide production of commercial quantities of one or more PUFAs. Consequently, there is a definite need for elongase enzymes, the genes encoding the enzymes, as well as recombinant methods of producing the enzymes.

In view of the above discussion, a definite need also exists for oils containing levels of PUFAs beyond those naturally present as well as those enriched in novel PUFAs. Such oils can be made by isolation and expression of elongase genes.

One of the most important long-chain PUFAs is eicosapentaenoic acid (EPA). EPA is found in fungi and also in marine oils. Docosahexaenoic acid (DHA) is another important long-chain PUFA. DHA is most often found in fish oil and can also be purified from mammalian brain tissue. Arachidonic acid (ARA) is a third important long-chain PUFA. ARA is found in filamentous fungi and can also be purified from mammalian tissues including the liver and the adrenal glands.

ARA, EPA and/or DHA, for example, can be produced via either the alternate 4-8 desaturase/Δ9-elongase pathway or the conventional Δ6 pathway (see FIG. 1). Elongases, which are active on substrate fatty acids in the conventional 46 pathway for the production of long-chain PUFAs, particularly ARA, EPA and DHA, have previously been identified. The conventional Δ6 pathway for converting LA to DGLA and ALA to ω3-ETA utilizes the Δ6-desaturase enzyme to convert LA to GLA, and ALA to stearidonic acid (SDA), and the Δ6-elongase enzyme to convert GLA to DGLA, and SDA to ω3-ETA. However, in certain instances, the alternate Δ8-desaturase/Δ9-elongase pathway may be preferred over the conventional Δ6 pathway. For example, if particular residual omega-6 or omega-3 fatty acid intermediates, such as GLA or SDA, are not desired during production of DGLA, ω3-ETA, ARA, EPA, ω3-docosapentaenoic acid, ω6-docosapentaenoic acid, ADA and/or DHA, the alternate Δ8-desaturase/Δ9-elongase pathway may be used as an alternative to the conventional Δ6 pathway, to bypass GLA and SDA formation.

In the present disclosure, a new source of Δ9-elongase has been identified for the production of long-chain PUFAs, in particular DGLA, ETA, ARA, EPA, ω3-docosapentaenoic acid, ω6-docosapentaenoic acid, ADA and/or DHA. The Δ9-elongase enzyme of the present disclosure converts, for example, LA to ω6-EDA, and ALA to ω3-ETrA. The production of DGLA from ω6-EDA, and ARA from DGLA, is then catalyzed by a Δ8-desaturase and a Δ5-desaturase, respectively.

SUMMARY OF THE DISCLOSURE

In one aspect, the present disclosure relates to an isolated nucleic acid molecule or fragment thereof comprising or complementary to an isolated nucleotide sequence encoding a polypeptide having elongase activity, wherein the amino acid sequence of the polypeptide has at least 68% sequence identity to an amino acid sequence selected from the group consisting of SEQ ID NO: 18 and SEQ ID NO: 20.

In another aspect, the present disclosure relates to an isolated nucleotide sequence or fragment thereof comprising or complementary to at least 68% of a nucleotide sequence selected from the group consisting of SEQ ID NO: 17 and SEQ ID NO: 19. The isolated nucleotide sequence or fragment thereof encodes a functionally active elongase which utilizes a polyunsaturated fatty acid as a substrate, and in particular a functionally active Δ9-elongase.

The nucleotide sequence may be from, for example, a *Euglenoid* sp., and may specifically be isolated from, for example, *Euglena deses Ehr*. CCMP 2916.

In another aspect, the present disclosure relates to a purified polypeptide encoded by the above-described isolated nucleotide sequence as well as a purified polypeptide which elongates polyunsaturated fatty acids containing unsaturation at the carbon 9 position and has at least 68% amino acid identity to an amino acid sequence selected from the group consisting of SEQ ID NO: 18 and SEQ ID NO: 20.

In still another aspect, the present disclosure relates to an expression vector. The expression vector comprises a nucleotide sequence operably linked to a regulatory sequence, wherein the nucleotide sequence comprises or si complementary to at least 68% of a nucleotide sequence selected from the group consisting of SEQ ID NO: 17 and SEQ ID NO: 19. The disclosure also relates to a host cell comprising this expression vector. The host cell may be, for example, a eukaryotic cell or a prokaryotic cell. Suitable eukaryotic cells and prokaryotic cells are set forth herein. The disclosure also relates to a transgenic seed comprising the expression vector.

In another aspect, the present disclosure relates to a plant cell, plant seed, plant or plant tissue comprising the above-described expression vector, wherein expression of the nucleotide sequence of the expression vector results in production of at least one polyunsaturated fatty acid by the plant cell, plant or plant tissue. The polyunsaturated fatty acid may be, for example, selected from the group consisting of ω6-EDA and ω3-ETrA, and combinations thereof. The present disclosure also includes one or more plant oils or fatty acids expressed by the above plant cell, plant seed, plant or plant tissue.

Furthermore, the present disclosure relates to a method of producing a Δ9-elongase. The method comprises the steps of: a) isolating a nucleotide sequence comprising or complementary to at least 68% of a nucleotide sequence selected from the group consisting of SEQ ID NO: 17 and SEQ ID NO: 19; b) constructing an expression vector comprising: i) the isolated nucleotide sequence operably linked to ii) a regulatory sequence; and c) introducing the expression vector into a host cell for a time and under conditions sufficient for expression of the Δ9-elongase, as appropriate. The host cell may be, for example, a eukaryotic cell or a prokaryotic cell. In particular, the eukaryotic cell may be, for example, a mammalian cell, an insect cell, a plant cell or a fungal cell. The plant cell may be from an oilseed plant selected from the group consisting of soybean, *Brassica* species, safflower, sunflower, maize, cotton, and flax.

Additionally, the present disclosure relates to a method for producing a polyunsaturated fatty acid comprising the steps of: a) isolating a nucleotide sequence comprising or complementary to at least 68% of a nucleotide sequence selected from the group consisting of SEQ ID NO: 17 and SEQ ID NO: 19; b) constructing an expression vector comprising the isolated nucleotide sequence operably linked to a regulatory sequence; c) introducing the expression vector into a host cell under time and conditions sufficient for expression of Δ9-elongase; and d) exposing the expressed Δ9-elongase to a substrate polyunsaturated fatty acid in order to convert the substrate polyunsaturated fatty acid to a first product polyunsaturated fatty acid. The "substrate" polyunsaturated fatty acid is, for example, LA or ALA, and the "first product" polyunsaturated fatty acid is, for example, ω6-EDA or ω3-ETrA, respectively. This method may further comprise the step of exposing the first product polyunsaturated fatty acid to at least one desaturase, at least one additional elongase, or combinations thereof, in order to convert the first product polyunsaturated fatty acid to a second or subsequent polyunsaturated fatty acid. The second or subsequent product polyunsaturated fatty acid may be, for example, DGLA or ω3-ETA, ARA, EPA, DPA, DHA, or combinations thereof.

In another aspect, the present disclosure relates to a method for producing a polyunsaturated fatty acid in a host cell comprising the steps of: a) isolating a nucleotide sequence comprising or complementary to at least 68% of a nucleotide sequence selected from the group consisting of SEQ ID NO: 17 and SEQ ID NO: 19; b) constructing an expression vector comprising the isolated nucleotide sequence operably linked to a regulatory sequence; c) introducing i) the expression vector and ii) at least one additional recombinant DNA construct comprising an isolated nucleotide sequence encoding a Δ8-desaturase and operably linked to at least one regulatory sequence, into a host cell for a time and under conditions sufficient for expression of a Δ9-elongase and the Δ8-desaturase; and d) exposing the expressed Δ9-elongase and the Δ8-desaturase to a substrate polyunsaturated fatty acid selected from the group consisting of LA, ALA, and combinations thereof in order to convert the substrate polyunsaturated fatty acid to a first product polyunsaturated fatty acid. The first product polyunsaturated fatty acid may be, for example, DGLA, ω3-ETA, or combinations thereof. This method may further comprise the step of exposing the first product polyunsaturated fatty acid to at least one desaturase, at least one additional elongase, or combinations thereof, in order to convert the first product polyunsaturated fatty acid to a second or subsequent polyunsaturated fatty acid. The second or subsequent product polyunsaturated fatty acid may be, for example, ARA, EPA, DPA, DHA, or combinations thereof. In one aspect, this method may further comprise introducing into the host cell a recombinant DNA construct comprising i) an isolated nucleotide sequence encoding a Δ5-desaturase operably linked to ii) a regulatory sequence. The host cell may be as described above.

In another aspect, the present disclosure relates to a method for producing a transgenic plant comprising transforming a plant cell with at least one isolated nucleotide sequence or fragment thereof comprising or complementary to at least 68% of a nucleotide sequence selected from the group consisting of SEQ ID NO: 17 and SEQ ID NO: 19, and regenerating a transgenic plant from the transformed plant cell. The plant cell may be from an oilseed plant selected from the group consisting of soybean, *Brassica* species, safflower, sunflower, maize, cotton, and flax. In another aspect, the present disclosure relates to a seed obtained from the transgenic plant produced by this method.

It should also be noted that each nucleotide and amino acid sequence referred to herein has been assigned a particular sequence identification number. The Sequence Listing (which is attached hereto), incorporated herein by reference, lists each such sequence and its corresponding number.

BRIEF DESCRIPTION OF THE DRAWINGS

FIGS. 2A and 2B show alignment of nucleotide sequences SEQ ID NO: 26 and SEQ ID NO: 27, which are nucleotide sequences of Eug-M07-ELO#10 and the Eug-M07-ELO#14 variant, respectively, cloned into the Bam HI/Hind III sites of vector pYX242, as discussed in Example 3. A box is drawn around variants.

FIGS. 3A and 3B show alignment of amino acid sequences of Δ9-elongase from *Euglena deses Ehr.* CCMP 2916 (Eug-M07-ELO-10) (SEQ ID NO: 18) with known Δ9-elongases from *Euglena gracialis* (SEQ ID NO: 4), *Isochrysis galbana* (SEQ ID NO: 2); Mouse Elov14 elongase (Accession # AAG47667; SEQ ID NO: 21), human ELOVL2 elongase (Accession # NP_060240; SEQ ID NO: 22), and *C. elegans* elongase (Ascession # AF244356; SEQ ID NO: 23). A box is drawn around invariant residues.

FIG. 4A shows the Δ9-elongase amino acid sequence from *Pavlova salina* (Accession #AAY15135; SEQ ID NO: 1).

FIG. 4B shows the Δ9-elongase amino acid sequence from *Isochrysis galbana* (Accession #AF390174; SEQ ID NO: 2).

FIG. 4C shows the Δ9-elongase amino acid sequence from *Eutreptiella* sp. (SEQ ID NO: 3).

FIG. 4D shows the Δ9-elongase amino acid sequence from *Euglena gracialis* (Accession #CAT16687; SEQ ID NO: 4).

FIG. 4E shows the Δ9-elongase amino acid sequence from *Euglena anabena* (SEQ ID NO: 5).

FIG. 5A shows the nucleotide sequence (SEQ ID NO: 6) of clone plate2_MO7, obtained as described in Example 1.

FIG. 5B shows the deduced amino acid sequence (SEQ ID NO: 7) of clone plate2_MO7, obtained as described in Example 1.

FIG. 6A shows the nucleotide sequence (SEQ ID NO: 13) of the plate2_MO7 gene fragment putative 3'-end, obtained as described in Example 2.

FIG. 6B shows the predicted amino acid sequence (SEQ ID NOs: 14 and 30-32) of the plate2_MO7 gene fragment putative 3'-end, obtained as described in Example 2. SEQ ID NOs: 14 and 30-32 are separated by an "*", which represents a stop codon.

FIG. 6C shows SEQ ID NO: 14.
FIG. 6D shows SEQ ID NO: 30.
FIG. 6E shows SEQ ID NO: 31.
FIG. 6F shows SEQ ID NO: 32.

FIG. 7A shows the nucleotide sequence (SEQ ID NO: 17) of the putative Δ9-elongase from *Euglena deses Ehr.* CCMP 2916 (Eug-M07-ELO#10), obtained as described in Example 3.

FIG. 7B shows the predicted amino acid sequence (SEQ ID NO: 18) encoded by the nucleotide sequence (SEQ ID NO: 17) of the putative Δ9-elongase from *Euglena deses Ehr.* CCMP 2916 (Eug-M07-ELO#10), obtained as described in Example 3.

FIG. 8A shows the nucleotide sequence (SEQ ID NO: 19) of a variant Δ9-elongase from *Euglena deses Ehr.* CCMP 2916 (Eug-M07-ELO#14), obtained as described in Example 3.

FIG. 8B shows the predicted amino acid sequence (SEQ ID NO: 20) encoded by nucleotide sequence (SEQ ID NO: 19) of the variant Δ9-elongase from *Euglena deses Ehr.* CCMP 2916 (Eug-M07-ELO#14), obtained as described in Example 3.

FIG. 9A shows the amino acid sequence from Mouse Elov14 elongase (Accession #AAG47667; SEQ ID NO: 21).

FIG. 9B shows the amino acid sequence from human ELOVL2 elongase (Accession #NP_060240; SEQ ID NO: 22).

FIG. 9C shows the amino acid sequence from *C. elegans* elongase (Accession #AF244356; SEQ ID NO: 23).

DETAILED DESCRIPTION OF THE DISCLOSURE

Figure 1:
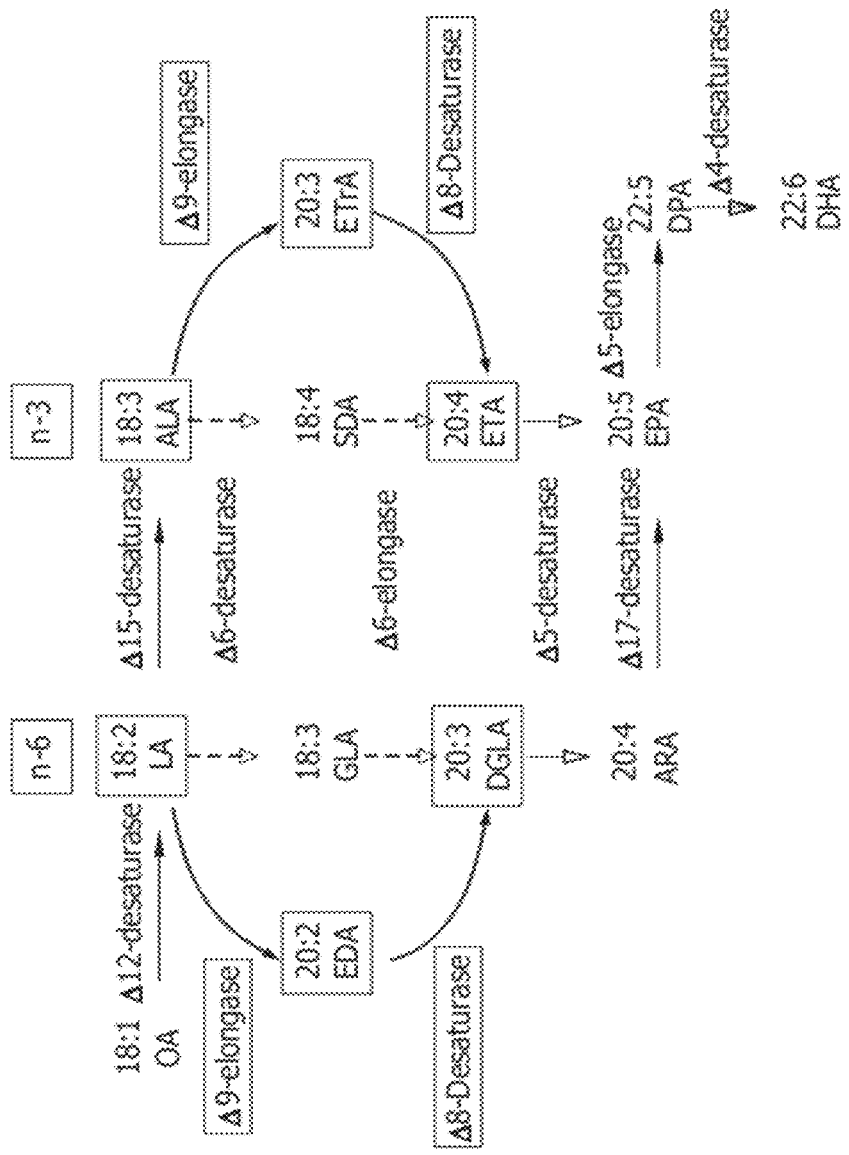
FIG. 1 shows the fatty acid biosynthetic pathway and the role of Δ9-elongase in this pathway.

The present disclosure is directed to the nucleotide (e.g., gene) and translated amino acid sequences of a Δ9-elongase gene from *Euglenoid* sp., for example, *Euglena deses Ehr.*, specifically *Euglena deses Ehr.* CCMP 2916. Furthermore, the present disclosure also includes uses of the gene and of the enzyme encoded by the gene. For example, the gene and corresponding enzyme may be used in the production of polyunsaturated fatty acids such as, for instance, ω6-EDA, ω3-EtrA, DGLA, ω3-ETA, ARA, EPA, ω3-docosapentaenoic acid, ω6-docosapentaenoic acid, ADA, DHA, or any combinations thereof, which may be added to pharmaceutical compositions, nutritional compositions and to other valuable products.

DEFINITIONS

As used herein, the singular forms "a" "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

Chimeric Construct: As used herein, the phrase "chimeric construct" refers to a combination of nucleic acid molecules that are not normally found together in nature. Accordingly, a chimeric construct may comprise regulatory sequences and coding sequences that are derived from different sources, or regulatory sequences and coding sequences derived from the same source, but arranged in a manner different than that normally found in nature.

Coding Sequence: As used herein, the term "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

Complementarity: As used herein, the term "complementarity" refers to the degree of relatedness between two DNA segments. It is determined by measuring the ability of the sense strand of one DNA segment to hybridize with the antisense strand of the other DNA segment, under appropriate conditions, to form a double helix. In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

Encoded by, Hybridization, and Stringent Conditions: As used herein, the phrase, "encoded by" refers to a nucleic acid sequence which codes for a polypeptide sequence, wherein the polypeptide sequence or a portion thereof contains an amino acid sequence of at least 3 consecutive amino acids, more preferably at least 8 consecutive amino acids, and even more preferably at least 15 consecutive amino acids from a polypeptide encoded by the nucleic acid sequence.

The present disclosure also encompasses an isolated nucleotide sequence which encodes for an enzyme having PUFA elongase activity and that is hybridizable, under moderately stringent conditions, to a nucleic acid having a nucleotide sequence comprising or complementary to a nucleotide sequence comprising SEQ ID NO: 17 or SEQ ID NO: 19 (shown in FIGS. 7A and 8A, respectively). A nucleic acid molecule is "hybridizable" to another nucleic acid molecule when a single-stranded form of the nucleic acid molecule can anneal to the other nucleic acid molecule under the appropriate conditions of temperature and ionic strength (See, Sambrook et al., Molecular Cloning: A Laboratory Manual, Second Edition (1989), Cold Spring Harbor Laboratory Press, Cold Spring Harbor, New York)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known to those skilled in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (See, Sambrook et al., supra). For hybridization with shorter nucleic acids, the position of mismatches becomes more important, and the length of the oligonucleotide determines its specificity (See, Sambrook et al., supra).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. An example of low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. An example of moderate stringency conditions include hybridization in 40 to 45% formamide, 1 M NaCl, 1% SDS at 37° C., and a wash in 0.5× to 1×SSC at 55 to 60° C. An example of high stringency conditions include hybridization in 50% formamide, 1 M NaCl, 1% SDS at 37° C., and a wash in 0.1×SSC at 60 to 65° C.

Exon: As used herein, the term "exon" refers to a portion of the sequence of a gene that is transcribed and is found in the mature messenger RNA derived from the gene, but is not necessarily a part of the sequence that encodes the final gene product.

Expression, Antisense Inhibition, and Co-suppression: As used herein, the term "expression", refers to the production of a functional end-product. Expression of a gene involves transcription of the gene and translation of the mRNA into a precursor or mature protein.

As used herein, the phrase "antisense inhibition" refers to the production of antisense RNA transcripts capable of suppressing the expression of the target protein.

As used herein, the term "co suppression" refers to the production of sense RNA transcripts capable of suppressing the expression of identical or substantially similar foreign or endogenous genes (See, U.S. Pat. No. 5,231,020).

Fragment or Subfragment that is Functionally Equivalent: The terms "fragment or subfragment that is functionally equivalent" and "functionally equivalent fragment or subfragment", used interchangeably herein, refer to a portion or subsequence of an isolated nucleic acid molecule in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense inhibition by linking a nucleic acid fragment or subfragment thereof, whether or not it encodes an active enzyme, in the appropriate orientation relative to a plant promoter sequence.

Gene, Native Gene, Foreign Gene, and Transgene: As used herein, the term "gene" refers to a nucleic acid molecule that expresses a specific protein, including regulatory sequences preceding (5' non-coding sequences) and following (3' non-coding sequences) the coding sequence.

As used herein, the phrase "native gene" refers to a gene as found in nature with its own regulatory sequences.

A "foreign" gene refers to a gene not normally found in the host organism, but that is introduced into the host organism by gene transfer. Foreign genes can comprise native genes inserted into a non-native organism, or chimeric constructs.

As used herein, the term "transgene" refers to gene that has been introduced into the genome by a transformation procedure.

*Gossypium* species: As used herein, the phrase "*Gossypium* species" refers to any plants of *Gossypium arboreum*, *Gossypium barbadense*, *Gossypium herbaceum*, *Gossypium hirsutum*, *Gossypium hirsutum* var *hirsutum*, *Gossypium hirsutum* var *marie-galante*, *Gossypium lapideum*, *Gossypium sturtianum*, *Gossypium thuberi*, *Gossypium thurberi*, *Gossypium tomentosum* or *Gossypium tormentosum*.

Homology: The terms "homology", "homologous", "substantially similar" and "corresponding substantially" are used interchangeably herein and refer to nucleic acid molecules wherein changes in one or more nucleotide bases does not affect the ability of the nucleic acid molecule to mediate gene expression or produce a certain phenotype. These terms also refer to modifications of the nucleic acid molecules of the instant disclosure such as a deletion or insertion of one or more nucleotides that do not substantially alter the functional properties of the resulting nucleic acid molecule relative to the initial, unmodified molecule. It is therefore understood, as those skilled in the art will appreciate, that the disclosure encompasses more than the specific exemplary sequences.

Host Cell: As used herein, the phrase "host cell" is meant a cell, which comprises an isolated nucleic acid sequence or fragment thereof of the present disclosure. Host cells may be prokaryotic cells (e.g. such as *Escherichia coli*, cyanobacteria and *Bacillus subtilis*), or eukaryotic cells (e.g. such as fungal, insect, plant or mammalian cells).

Examples of fungal cells that can be used are *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. A particularly preferred fungal cell is *Saccharomyces cerevisiae*.

Plant cells can be monocotyledonous or dicotyledonous plant cells. Particularly preferred plant cells are from oilseed plants such as *Glycine max* (e.g., soybean), a *Brassica* species, *Carthamus tinctorius* L. (e.g., safflower), *Helianthus annuus* (e.g., sunflower), *Zea mays* (e.g., maize), a *Gossypium* species (cotton) and *Linum usitatissimum* (e.g, flax).

Identity, Sequence Identity, and Percentage of Sequence Identity (% Identity): The terms "identity" or "sequence identity," used interchangeably herein, when used in the context of nucleotide or polypeptide sequences refer to the nucleic acid bases or amino acid residues in two sequences that are the same when aligned for maximum correspondence over a specified comparison window. Thus, identity is defined as the degree of sameness, correspondence or equivalence between the same strands (either sense or antisense) of two DNA or polypeptide segments.

"Percentage of sequence identity" or "% identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, *Appl. Math.* 2:482 (1981), by the algorithm of Needleman & Wunsch, *J. Mol. Biol.* 48:443 (1970), by the method of Pearson & Lipman, *Proc. Natl. Acad. Sci.* (USA) 85:2444 (1988) and by computer programs which implement the relevant algorithms (e.g., Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See, U.S. Pat. No. 5,912, 120). Useful examples of percent sequence identities include, but are not limited to, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. These identities can be determined using any of the programs described herein.

Indirectly or Directly: As used herein, the term "indirectly" when used in connection with the use of a gene and its corresponding enzyme in the production of polyunsaturated fatty acids, encompasses the situation where a first acid is converted to second acid (i.e., a pathway intermediate) by a first enzyme (e.g., LA to ω6-EDA, by, for example a Δ9-elongase) and then the second acid is converted to third acid by use of a second enzyme (e.g., ω6-EDA to DGLA by, for example, Δ8-desaturase).

As used herein, the term "directly" when used in connection with the use of a gene and its corresponding enzyme in the production of polyunsaturated fatty acids encompasses the situation where the enzyme directly converts a first acid to a second acid, wherein the second acid is then utilized in a composition (e.g., the conversion of LA to ω6-EDA by, for example a Δ9-elongase or ω3-ETrA to ω3-ETA by, for example a Δ8-desaturasae).

Intron: As used herein, the term "intron" refers to an intervening sequence in a gene that does not encode a portion of the protein sequence. Thus, such sequences are transcribed into RNA but are then excised and are not translated. The term is also used for the excised RNA sequences.

Isolated: As used herein, the term "isolated" refers to a nucleic acid molecule (DNA or RNA) or a protein or a biologically active portion thereof that is removed from its naturally occurring environment or source using routine techniques known in the art (e.g., from bacteria, algae, fungi, plants, vertebrates, mammals, etc.). Isolated nucleic acid molecules or proteins are substantially or essentially free from components that normally accompany or interact with the nucleic acid molecules or proteins in their naturally occurring environment.

Isolated Nucleic Acid Fragment or Isolated Nucleic Acid Sequence: As used herein, the phrase "isolated nucleic acid fragment" or "isolated nucleic acid sequence" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 consecutive nucleotides, preferably at least about 8 consecutive nucleotides, more preferably at least about 10 consecutive nucleotides, at least about 15 consecutive nucleotides, at least about 20 consecutive nucleotides, at least about 25 consecutive nucleotides, etc., identical or complementary to a region of the specified nucleotide sequence.) Nucleotides (usually found in their 5' monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

Mature and Precursor: As used herein, the term, "mature" when used in connection with the term "protein" refers to a post-translationally processed polypeptide; i.e., one from which any pre- or propeptides present in the primary translation product have been removed. As used herein, the term "precursor" when used in connection with the term "protein" refers to the primary product of translation of mRNA; i.e., with pre- and propeptides still present. Pre- and propeptides may be, but are not limited to, intracellular localization signals.

3' Non-Coding Sequences: As used herein, the phrase "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671 680.

Non-Naturally Occurring: As used herein, the phrase, "non-naturally occurring" refers to something that is artificial, not consistent with what is normally found in nature.

Operably Linked: As used herein, the phrase "operably linked" refers to the association of nucleic acid sequences on a single nucleic acid molecule so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

Plant: As used herein, the term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

Polymerase Chain Reaction or PCR: As used herein, the phrase "Polymerase Chain Reaction" or "PCR" refers to a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

PCR is a powerful technique used to amplify DNA millions of fold, by repeated replication of a template, in a short period of time (Mullis et al, *Cold Spring Harbor Symp. Quant. Biol.* 51:263 273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20 50) of melting the template at high temperature, allowing the primers to anneal to complementary sequences within the template and then replicating the template with DNA polymerase. The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

Promoter and Enhancer: As used herein, the term "promoter" refers to a DNA sequence capable of controlling the expression of a coding sequence or functional RNA. The promoter sequence consists of proximal and more distal upstream elements, the latter elements often referred to as enhancers.

As used herein, the term "enhancer" refers to a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters." New promoters of various types useful in plant cells are constantly being discovered; numerous examples may be found in the compilation by Okamuro and Goldberg, (1989) *Biochemistry of Plants* 15:1 82. It is further recognized that since in most cases the exact boundaries of regulatory sequences have not been completely defined, DNA molecules of some variation may have identical promoter activity.

Recombinant: As used herein, the term "recombinant" refers to an artificial combination of two otherwise separated segments of sequence, e.g., by chemical synthesis or by the manipulation of isolated segments of nucleic acids by genetic engineering techniques.

Recombinant Construct, Expression Construct, and Recombinant Expression Construct: The phrases "recombinant construct", "expression construct" and "recombinant expression construct" are used interchangeably herein and refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid molecules of the disclosure. The skilled artisan will also recognize that different independent transformation events will result in different levels and patterns of expression (Jones et al., (1985) *EMBO J.* 4:2411 2418; De Almeida et al., (1989) *Mol. Gen. Genetics* 218:78 86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

RNA transcript, Messenger RNA, cDNA, Functional RNA, and Endogenous RNA: As used herein, the phrase, "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

As used herein, the phrase "messenger RNA (mRNA)" refers to the RNA that is without introns and that can be translated into protein by the cell.

As used herein, the term "cDNA" refers to a DNA that is complementary to and synthesized from a mRNA template using the enzyme reverse transcriptase. The cDNA can be single-stranded or converted into the double-stranded form using the Klenow molecule of DNA polymerase I. "Sense"

RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence.

As used herein, the phrase, "functional RNA" refers to antisense RNA, ribozyme RNA, or other RNA that may not be translated but yet has an effect on cellular processes.

The terms "complement" and "reverse complement" are used interchangeably herein with respect to mRNA transcripts, and are meant to define the antisense RNA of the message.

As used herein, the phrase "endogenous RNA" refers to any RNA which is encoded by any nucleic acid sequence present in the genome of the host prior to transformation with the recombinant construct of the present disclosure, whether naturally-occurring or non-naturally occurring, i.e., introduced by recombinant means, mutagenesis, etc.

Similarity: The term "similarity," when referring to the "similarity" between two amino acid sequences, proteins or polypeptides, refers to the presence of a series of identical as well as conserved amino acid residues in both sequences. The higher the degree of similarity between two amino acid sequences, the higher the correspondence, sameness or equivalence of the two sequences.

Stable Transformation, Transient Transformation, and Transformation: As used herein, the phrase "stable transformation" refers to the transfer of a nucleic acid molecule into a genome of a host organism, including both nuclear and organellar genomes, resulting in genetically stable inheritance.

In contrast, as used herein, the phrase "transient transformation" refers to the transfer of a nucleic acid molecule into the nucleus, or DNA-containing organelle, of a host organism resulting in gene expression without integration or stable inheritance. Host organisms containing the transformed nucleic acid molecules are referred to as "transgenic" organisms. The preferred method of cell transformation of rice, corn and other monocots is the use of particle-accelerated or "gene gun" transformation technology (Klein et al., (1987) *Nature* (London) 327:70 73; U.S. Pat. No. 4,945,050), or an *Agrobacterium*-mediated method using an appropriate Ti plasmid containing the transgene (Ishida Y. et al., (1996) *Nature Biotech.* 14:745 750).

As used herein, the term "transformation" refers to both stable transformation and transient transformation.

Translation Leader Sequence: As used herein, the phrase "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

All patents, patent publications and priority documents cited herein are hereby incorporated by reference in their entirety.

The Δ9-Elongase Gene and Enzyme Encoded Thereby

The enzyme encoded by the Δ9-elongase gene of the present disclosure is essential in the production, via the alternate Δ8-desaturase/Δ9-elongase pathway, of long-chain polyunsaturated fatty acids (LC-PUFAs), having a length of 20 or greater carbons. The nucleotide sequence of the isolated *Euglena deses Ehr.* CCMP 2916 Δ9-elongase gene is shown in FIG. 7A, and the predicted amino acid sequence of the corresponding protein is shown in FIG. 7B.

The conversion of LA to DGLA and ALA to ω3-ETA using a Δ9-elongase enzyme and a Δ8-desaturase enzyme is referred to as the alternate Δ8-desaturase/Δ9-elongase pathway. The conventional Δ6 pathway for converting LA to DGLA and ALA to ω3-ETA utilizes a Δ6-desaturase enzyme to convert LA to GLA, and ALA to SDA, and a Δ6-elongase to convert GLA to DGLA, and SDA to ω3-ETA, respectively. In either pathway, the production of ARA or EPA is then catalyzed by, for example, a Δ5-desaturase. DHA, for example, may be produced upon the conversion of EPA to ω3-docosapentaenoic acid (DPA), and ω3-docosapentaenoic acid to DHA, utilizing, for example, a Δ5-elongase and a Δ4-desaturase, respectively.

Although, for example, DGLA, ω3-ETA, ARA, EPA, ω3-docosapentaenoic acid, ω6-docosapentaenoic acid, ADA and/or DHA can be produced via either the alternate Δ8-desaturase/Δ9-elongase pathway or the conventional 46 pathway, in certain instances, the alternate Δ8-desaturase/Δ9-elongase pathway may be preferred over the conventional Δ6 pathway. For example, if particular residual omega-6 or omega-3 fatty acid intermediates, such as GLA or SDA, are not desired during production of DGLA, ω3-ETA, ARA, EPA, ω3-docosapentaenoic acid, ω6-docosapentaenoic acid, ADA and/or DHA, the alternate Δ8-desaturase/Δ9-elongase pathway may be used as an alternative to the conventional 46 pathway, to bypass GLA and SDA formation.

As discussed above, Δ9-elongase is a necessary enzyme in the alternate Δ8-desaturase/Δ9-elongase pathway. EPA, for example, cannot be synthesized via the alternate Δ8-desaturase/Δ9-elongase pathway without the Δ9-elongase gene and enzyme encoded thereby. As shown in FIG. 1, the isolated Δ9-elongase enzyme of the present disclosure converts, for example, ALA to ω3-ETrA and LA to ω6-EDA. The production of ω3-ETA from ω3-ETrA, and EPA from ω3-ETA is then catalyzed by, for example, a Δ8-desaturase and a Δ5-desaturase, respectively. As a result of using the alternate Δ8-desaturase/49-elongase pathway, the intermediate GLA and SDA fatty acids are bypassed.

It should be noted that the present disclosure also encompasses nucleotide sequences (and the corresponding encoded proteins) having sequences comprising, consisting of, or complementary to at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in sequence (i.e., having sequence identity to) SEQ ID NO: 17 (i.e., the isolated nucleotide sequence of the Δ9-elongase gene of *Euglena deses Ehr.* CCMP 2916) or SEQ ID NO: 19 (i.e., a variant Δ9-elongase gene of *Euglena deses Ehr.* CCMP 2916). Such sequences may be from human sources as well as other non-human sources (e.g., *C. elegans* or mouse).

Furthermore, the present disclosure also encompasses fragments and derivatives comprising or consisting of the nucleotide sequence of SEQ ID NO: 17 (shown in FIG. 7A) or SEQ ID NO: 19 (shown in FIG. 8A)), as well as of the sequences from other sources, and having the above-described complementarity or correspondence. Functional equivalents of the above-sequences (i.e., sequences having Δ9-elongase activity) are also encompassed by the present disclosure.

Fragments derived from SEQ ID NO: 17 or SEQ ID NO: 19 can have a length comprising or consisting of 10 to about 780 nucleotides, 10 to about 700 nucleotides, 10 to about 650 nucleotides, 10 to about 500 nucleotides, 10 to about 250 nucleotides, 10 to about 100 nucleotides, 10 to about 50 nucleotides, or 15 to 40 nucleotides. In one aspect, the fragments of SEQ ID NO: 17 and SEQ ID NO: 19 encode a polypeptide having Δ9-elongase activity. In another aspect, fragments of the SEQ ID NO: 17 and SEQ ID NO: 19 can be used as primers and probes. Methods of making primers and probes are well known to those skilled in the art. Such primers and probes can have a length of 10 to 50 nucleotides, preferably from 15 to 40 nucleotides.

Variants of the nucleotide sequence of SEQ ID NO: 17 or SEQ ID NO: 19 are also contemplated herein. Such variants may contain one or more base pair additions, substitutions, or deletions. Non-limiting examples of nucleotide variants of SEQ ID NO: 17 encompassed by the present disclosure are shown in Table A below. One specific example of a variant of SEQ ID NO: 17 is SEQ ID NO: 19 (see FIG. 8A).

TABLE A

Sequence Substitution
(SEQ ID NO: 17 ⇒
SEQ ID NO: 19)

$GCT_{24} \Rightarrow GCC_{24}$
$GC_{83}C \Rightarrow GT_{83}C$
$G_{232}TA \Rightarrow A_{232}TA$
$A_{301}TG \Rightarrow T_{301}TG$
$C_{310}TC \Rightarrow A_{310}TC$
$ACA_{630} \Rightarrow ACT_{630}$
$AAA_{750} \Rightarrow AAG_{750}$ The present disclosure also encompasses nucleotide sequences from other sources, and having the above-described complementarity or correspondence to SEQ ID NO: 17 or SEQ ID NO: 19. Functional equivalents of SEQ ID NO: 17 or SEQ ID NO: 19 (i.e., sequences having Δ9-elongase activity) are also encompassed by the present disclosure.

The present disclosure also encompasses nucleotide sequences or fragments thereof encoding a polypeptide having Δ9-elongase activity, wherein the amino acid sequence of said polypeptide has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99° A sequence identity to an amino acid sequence comprising SEQ ID NO: 18 or SEQ ID NO: 20. Such sequences may be from human sources as well as other non-human sources (e.g., *C. elegans* or mouse).

The disclosure also includes an isolated and/or purified polypeptide which elongates polyunsaturated fatty acids containing unsaturation at the carbon 9 position (i.e., has Δ9-elongase activity) and has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% similarity or identity to the amino acid sequence (i.e., SEQ ID NO: 18 (shown in FIG. 7B) or SEQ ID NO: 20 (shown in FIG. 8B)). Specifically, the present disclosure includes a purified polypeptide having an amino acid sequence of SEQ ID NO: 18 or SEQ ID NO: 20.

Fragments of the polypeptide having the sequence of SEQ ID NO: 18 or SEQ ID NO: 20 are also contemplated herein. Such fragments can have a length comprising or consisting of 10 to about 260 consecutive amino acids, 10 to about 200 consecutive amino acids, 10 to about 100 consecutive amino acids, 10 to about 50 consecutive amino acids, 10 to about 40 consecutive amino acids, 10 to about 30 consecutive amino acids, or 10 to about 20 consecutive amino acids.

Variants of the polypeptide having the sequence of SEQ ID NO: 18 or SEQ ID NO: 20 are also contemplated herein. Such variants may contain one or more amino acid additions, substitutions, or deletions. Non-limiting examples of amino acid variants of SEQ ID NO: 18 encompassed by the present disclosure are shown in Table B below. One specific example of a variant of SEQ ID NO: 18 is SEQ ID NO: 20 (see FIG. 8B).

Amino Acid Substitution
(SEQ ID NO: 18 ⇒
SEQ ID NO: 20)

$A_{28} \Rightarrow V_{28}$
$V_{78} \Rightarrow I_{78}$
$M_{101} \Rightarrow L_{101}$
$L_{104} \Rightarrow I_{104}$ Production of the Δ9-Elongase Enzyme Once the nucleic acid (e.g., gene) encoding the Δ9-elongase enzyme has been isolated and/or purified, it may then be introduced into either a prokaryotic or eukaryotic host cell through the use of a vector or construct. The vector, for example, a bacteriophage, cosmid, or plasmid, may comprise the nucleotide sequence encoding the Δ9-elongase enzyme, as well as any regulatory sequence (e.g., promoter) which is functional in the host cell and is able to elicit expression of the Δ9-elongase encoded by the nucleotide sequence. The regulatory sequence is in operable association with or operably linked to the nucleotide sequence. (As noted above, regulatory is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual,* 2nd ed., Vol. 1-3, ed. Sambrook et al., Cold Spring Harbor Laboratory Press (1989)). The host cell is then cultured under suitable conditions permitting expression of the genes leading to the production of the desired PUFA, which is then recovered and purified using routine techniques known in the art.

Examples of suitable prokaryotic host cells include, but are not limited to, bacteria such as *Escherichia coli, Bacillus subtilis* as well as cyanobacteria such as *Spirulina* spp. (i.e., blue-green algae). The eukaryotic cell may be, for example, a mammalian cell, an insect cell, a plant cell or a fungal cell. The fungal cell may be, for example, *Saccharomyces* spp., *Candida* spp., *Lipomyces* spp., *Yarrowia* spp., *Aspergillus* spp., *Penicillium* spp., *Neurospora* spp., *Kluyveromyces* spp., *Hansenula* spp., *Trichoderma* spp., or *Pichia* spp. In particular, the fungal cell may be a yeast cell such as, for example, *Saccharomyces* spp., *Candida* spp., *Hansenula* spp. and *Pichia* spp. The yeast cell may also be *Saccharomyces cerevisiae*. The plant cell includes, but is not limited to, plant cells from oilseed plants such as *Glycine max* (e.g., soybean), a *Brassica* species, *Carthamus tinctorius* L. (e.g., safflower), *Helianthus annus* (e.g., sunflower), *Zea mays* (e.g., maize), a *Gossypium* species (e.g., cotton), and *Linum usitatissimum* (e.g., flax).

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the 49-elongase enzyme and ultimately the PUFA(s) of interest. More specifically, once the above-described construct is created, it may be inserted into the pronucleus of an embryo. The embryo may then be implanted into a recipient female. Alternatively, a nuclear transfer method could also be utilized (Schnieke, et al., *Science* 278:2130-2133 (1997)). Gestation and birth are then permitted (see, e.g., U.S. Pat. No. 5,750,176 and U.S. Pat. No. 5,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene encoding the desired desaturase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of a Δ9-elongase polypeptide, functional transcriptional and translational initiation and termination regions are operably linked to the DNA encoding the elongase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,188,958, and 5,589,379.

Alternatively, the expressed protein can be an enzyme which produces a product which may be incorporated, either directly or upon further modifications, into a fluid fraction from the host plant. Expression of a Δ9-elongase gene, or antisense Δ9-elongase transcripts, can alter the levels of specific PUFAs, or derivatives thereof, found in plant parts and/or plant tissues.

The Δ9-elongase polypeptide coding region may be expressed either by itself or with other genes (e.g., a gene encoding a Δ8-desaturase, a gene encoding a Δ5-desaturase, a gene encoding a Δ17-desaturase, a gene encoding a Δ5-elongase, and/or a gene encoding a Δ4-desaturase), in order to produce tissues and/or plant parts containing higher proportions of desired PUFAs or in which the PUFA composition more closely resembles that of human breast milk (see WO 95/24494). The termination region may be derived from the 3' region of the gene from which the initiation region was obtained or from a different gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the Δ9-elongase enzyme which may, in turn, be utilized in the production of polyunsaturated fatty acids. More specifically, desired PUFAS can be expressed in seed. Methods of isolating seed oils are known in the art. Thus, in addition to providing a source for PUFAs, seed oil components may be manipulated through the expression of the Δ9-elongase gene, as well as perhaps desaturase genes (e.g., Δ8-desaturase, Δ17-desaturase, Δ5-desaturases, Δ4-desaturase, etc.) and other elongase genes (e.g., Δ5-elongase, etc.), in order to provide seed oils that can be added to nutritional compositions, pharmaceutical compositions, animal feeds and cosmetics. Once again, a vector which comprises a DNA sequence encoding the Δ9-elongase operably linked to a promoter, will be introduced into the plant tissue or plant for a time and under conditions sufficient for expression of the Δ9-elongase gene. The vector may also comprise one or more genes that encode other enzymes, for example, Δ4-desaturase, Δ5-desaturase, Δ6-desaturase, Δ10-desaturase, Δ12-desaturase, Δ15-desaturase, Δ17-desaturase, Δ19-desaturase, Δ6-elongase, and/or Δ5-elongase. The plant tissue or plant may produce the relevant substrate upon which the enzymes act or a vector encoding enzymes which produce such substrates may be introduced into the plant tissue, plant cell or plant. In addition, substrate may be sprayed on plant tissues expressing the appropriate enzymes. Using these various techniques, one may produce PUFAs by use of a plant cell, plant tissue or plant. It should also be noted that the disclosure also encompasses a transgenic plant comprising the above-described vector, wherein expression of the nucleotide sequence of the vector results in production of a polyunsaturated fatty acid in, for example, the seeds of the transgenic plant.

The regeneration, development, and cultivation of plants from single plant protoplast transformants or from various transformed explants is well known in the art (Weissbach and Weissbach, In: *Methods for Plant Molecular Biology*, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *BiolTechnology* 6:923 (1988); Christou et al., *Plant Physiol.* 87:671 674 (1988)); *Brassica* (U.S. Pat. No. 5,463,174); peanut (Cheng et al., *Plant Cell Rep.* 15:653 657 (1996), McKently, et al., *Plant Cell Rep.* 14:699 703 (1995)); papaya; and pea (Grant et al., *Plant Cell Rep.* 15:254 258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603 618 (1990), Fromm et al., *BiolTechnology* 8:833 (1990), Koziel et al., *BiolTechnology* 11: 194, (1993), Armstrong et al., *Crop Science* 35:550 557 (1995)); oat (Somers et al., *BiolTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135 1148, (1996); Abedinia et al., *Aust. J. Plant Physiol.* 24:133 141 (1997); Zhang and Wu, *Theor. Appl. Genet.* 76:835 (1988); Zhang et al. *Plant Cell Rep.* 7:379, (1988); Battraw and Hall, *Plant Sci.* 86:191 202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454 457 (1988); Marcotte et al., *Plant Cell* 1:523 532 (1989); McCarty et al., *Cell* 66:895 905 (1991); Hattori et al., *Genes Dev.* 6:609 618 (1992); Goff et al., *EMBO J.* 9:2517 2522 (1990)).

Transient expression systems may be used to functionally dissect gene constructs (see generally, Maliga et al., *Methods in Plant Molecular Biology*, Cold Spring Harbor Press (1995)). It is understood that any of the nucleic acid molecules of the present disclosure can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular *Cloning: A Laboratory Manual*, Cold Spring Harbor Press (1989); Maliga et al., *Methods in Plant Molecular Biology*, Cold Spring Harbor Press (1995); Birren et al., *Genome Analysis Detecting Genes*, 1, Cold Spring Harbor, N.Y. (1998); Birren et al., *Genome Analysis: Analyzing DNA*, 2, Cold Spring Harbor, N.Y. (1998); *Plant Molecular Biology: A Laboratory Manual*, eds. Clark, Springer, New York (1997)).

The substrates which may be produced by the host cell either naturally or transgenically, as well as the enzymes which may be encoded by DNA sequences present in the vector which is subsequently introduced into the host cell, are shown in FIG. 1.

In view of the above, the present disclosure encompasses a method of producing the Δ9-elongase enzyme comprising the steps of: 1) isolating a nucleotide sequence comprising or complementary to at least 68% of the nucleotide sequence encoding the Δ9-elongase enzyme (e.g., a nucleotide sequence selected from the group consisting of SEQ ID NO: 17 and SEQ ID NO: 19); 2) constructing an expression vector comprising the nucleotide sequence operably linked to a regulatory sequence; and 3) introducing the vector into a host cell under time and conditions sufficient for the production of the Δ9-elongase enzyme.

The present disclosure also encompasses a method of producing polyunsaturated fatty acids. In one aspect, the method involves: 1) isolating a nucleotide sequence comprising or complementary to at least 68% of the nucleotide sequence encoding the Δ9-elongase enzyme (e.g., a nucleotide sequence selected from the group consisting of SEQ ID NO: 17 and SEQ ID NO: 19); 2) constructing an expression vector comprising the nucleotide sequence operably linked to a regulatory sequence; 3) introducing the expression vector into a host cell under time and conditions sufficient for the production of a Δ9-elongase enzyme; and 4) exposing the expressed Δ9-elongase to a substrate polyunsaturated fatty acid in order to convert the substrate polyunsaturated fatty acid to a first product polyunsaturated fatty acid. Examples of substrate PUFAs include LA, ALA, and combinations thereof. Examples of first product polyunsaturated fatty acid that can be produced by this method are ω6-EDA, ω3-ETrA, or both ω6-EDA and ω3-ETrA. For example, when LA is exposed to a Δ9-elongase enzyme, it is converted to ω6-EDA. In another example, when ALA is exposed to a Δ9-elongase enzyme, it is converted to ω3-ETrA.

The method can further involve the step(s) of exposing the first product polyunsaturated fatty acid to at least one desaturase, at least one additional elongase, or combinations thereof, and optionally repeating this step (i.e., exposing the second or subsequent product polyunsaturated fatty acid to a desaturase or elongase (which can be the same or different from any previously used desaturase or elongase) to convert the first product polyunsaturated fatty acid to a second or subsequent (e.g., third, fourth, fifth, sixth, etc.) product polyunsaturated fatty acid). This step can be repeated as many times as necessary until the desired product polyunsaturated fatty acid is obtained. For example, if the first product polyunsaturated fatty acid is ω6-EDA, the method can further comprise exposing ω6-EDA to, for example, Δ8-desaturase which converts the ω6-EDA to DGLA (a second product polyunsaturated fatty acid). The DGLA then may optionally be converted to ARA (a third product polyunsaturated fatty acid) by exposing the DGLA to, for example, Δ5-desaturase. The ARA can then be exposed to a Δ17-desaturase to produce EPA (a fourth product polyunsaturated fatty acid). Still further, optionally the EPA can be exposed to a Δ5-elongase to produce DPA (a fifth product polyunsaturated fatty acid). The DPA can then optionally be exposed to a Δ4-desaturase to produce DHA (a sixth product polyunsaturated fatty acid). In another example, if the first product polyunsaturated fatty acid is ω3-ETrA, the method can further comprise exposing the ω3-ETrA to, for example, Δ8-desaturase which converts the ω3-ETrA to ETA (a second product polyunsaturated fatty acid). The ETA may then be converted to EPA (a third product polyunsaturated fatty acid) by exposing the ETA to, for example, Δ5-desaturase. The EPA may be further converted to other polyunsaturated fatty acids as described above.

In another aspect, the method involves: 1) isolating a nucleotide sequence comprising or complementary to at least 68% of a nucleotide sequence encoding the Δ9-elongase enzyme (e.g., a nucleotide sequence selected from the group consisting of SEQ ID NO: 17 and SEQ ID NO: 19); 2) constructing an expression vector comprising the isolated nucleotide sequence operably linked to a regulatory sequence; 3) introducing the expression vector and at least one additional recombinant DNA construct comprising an isolated nucleotide sequence encoding a Δ8-desaturase and operably linked to at least one regulatory sequence into a host cell for a time and under conditions sufficient for expression of a Δ9-elongase and the 48-desaturase; and 4) exposing the expressed Δ9-elongase and the Δ8-desaturase to a substrate polyunsaturated fatty acid selected from the group consisting of LA, ALA, and combinations thereof, in order to convert the substrate polyunsaturated fatty acid to a first product polyunsaturated fatty acid. Examples of the first product polyunsaturated fatty acid include DGLA, ω3-ETA, and combinations thereof. Furthermore, the method can further involve the step(s) of exposing the first product polyunsaturated fatty acid to at least one additional desaturase or at least one additional elongase and, optionally, repeating this step (namely, exposing the second or subsequent product polyunsaturated fatty acid to a desaturase or elongase (which can be the same or different from any desaturase or elongase used previously)) to convert the first product polyunsaturated fatty acid (e.g., DGLA and/or ω3-ETA) to a second or subsequent (e.g., third, fourth, fifth, sixth, etc.) product polyunsaturated fatty acid. This step can be repeated as many times as necessary until the desired product polyunsaturated fatty acid is obtained. In one aspect, the method further includes introducing into the host cell a recombinant DNA construct comprising an isolated nucleotide sequence encoding a Δ5-desaturase operably linked to a regulatory sequence.

Thus, Δ9-elongase may be used in the production of polyunsaturated fatty acids which may be used, in turn, for particular beneficial purposes, or may be used in the production of other PUFAs.

Uses of the Δ9-Elongase Gene

As noted above, the Δ9-isolated elongase gene and the Δ9-elongase enzyme encoded thereby have many uses. For example, the gene and corresponding enzyme may be used indirectly or directly in the production of polyunsaturated fatty acids, for example, Δ9-elongase may be used in the production of ω6-EDA, ω3-ETrA, DGLA, ω3-ETA, ARA, EPA, ω3-docosapentaenoic acid, ω6-docosapentaenoic acid, ADA and/or DHA. "Directly" is meant to encompass the situation where the enzyme directly converts the acid to another acid, the latter of which is utilized in a composition (e.g., the conversion of LA to ω6-EDA). "Indirectly" is meant to encompass the situation where an acid is converted to another acid (i.e., a pathway intermediate) by the enzyme (e.g., LA to ω6-EDA) and then the latter acid is converted to another acid by use of a non-elongase enzyme (e.g., ω6-EDA to DGLA by, for example, Δ8-desaturase. These polyunsaturated fatty acids (i.e., those produced either directly or indirectly by activity of the Δ9-elongase enzyme) may be added to, for example, nutritional compositions, pharmaceutical compositions, cosmetics, and animal feeds, all of which are encompassed by the present disclosure. These uses are described, in detail, below.

Nutritional Compositions

The present disclosure includes nutritional compositions. Such compositions, for purposes of the present disclosure, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present disclosure comprises at least one oil or acid produced directly or indirectly by use of the Δ9-elongase gene, as described herein, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition of the disclosure include but are not limited to soy proteins, electrodialysed whey, electrodialysed skim milk, milk whey, or the hydrolysates of these proteins.

With respect to vitamins and minerals, the following may be added to the nutritional compositions of the present disclosure: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present disclosure will be of semi-purified or purified origin. By semi-purified or purified is meant a material which has been prepared by purification of a natural material or by synthesis.

Examples of nutritional compositions of the present disclosure include but are not limited to infant formulas, dietary supplements, dietary substitutes, and rehydration compositions. Nutritional compositions of particular interest include but are not limited to those utilized for enteral and parenteral supplementation for infants, specialty infant formulas, supplements for the elderly, and supplements for those with gastrointestinal difficulties and/or malabsorption.

The nutritional composition of the present disclosure may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present disclosure, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present disclosure, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art.

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or acid produced in accordance with the present disclosure may be added to any of these formulas.

The energy density of the nutritional compositions of the present disclosure, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present disclosure. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present disclosure, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. Thus, fatty acids such as ARA, EPA and/or DHA, produced in accordance with the present disclosure, can be used to alter, for example, the composition of infant formulas in order to better replicate the PUFA content of human breast milk or to alter the presence of PUFAs normally found in a non-human mammal's milk. In particular, a composition for use in a pharmacologic or food supplement, particularly a breast milk substitute or supplement, will preferably comprise one or more of ARA, EPA, DGLA, and DHA. More preferably, the oil will comprise from about 0.3 to 30% ARA, and from about 0.2 to 30% DGLA.

Parenteral nutritional compositions comprising from about 2 to about 30 weight percent fatty acids calculated as triglycerides are encompassed by the present disclosure. Other vitamins, particularly fat-soluble vitamins such as vitamin A, D, E and L-carnitine can optionally be included. When desired, a preservative such as alpha-tocopherol may be added in an amount of about 0.1% by weight.

In addition, the ratios of ARA and DGLA can be adapted for a particular given end use. When formulated as a breast milk supplement or substitute, a composition which comprises one or more of ARA, DGLA and GLA will be provided in a ratio of about 1:19:30 to about 6:1:0.2, respectively. For example, the breast milk of animals can vary in ratios of ARA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as EDA and DGLA to ARA can be used to precisely control the PUFA ratios. For example, a 5% to 10% conversion rate of DGLA to ARA can be used to produce an ARA to DGLA ratio of about 1:19, whereas a conversion rate of about 75% to 80% can be used to produce an ARA to DGLA ratio of about 6:1. Therefore, whether in a cell culture system or in a host animal, regulating the timing, extent and specificity of elongase expression, as well as the expression of desaturases (such as but not limited to Δ8-desaturases) and other elongases, can be used to modulate PUFA levels and ratios. The PUFAs/acids produced in accordance with the present disclosure (e.g., ARA and EPA) may then be combined with other PUFAs/acids (e.g., DGLA) in the desired concentrations and ratios.

Additionally, PUFA produced in accordance with the present disclosure or host cells containing them may also be used as animal food supplements to alter an animal's tissue or milk fatty acid composition to one more desirable for human or animal consumption.

Examples of some of the nutritional supplements, infant formulations, nutritional substitutes and other nutritional solutions that employ the polyunsaturated fatty acids produced pursuant to the present disclosure are described below.

Infant Formulations: Examples of infant formulations include, but are not limited to, Isomil® Soy Formula with Iron, Isomil® DF Soy Formula For Diarrhea, Isomil® Advance® Soy Formula with Iron, Isomil® Advance® 20 Soy Formula With Iron Ready To Feed, Similac® Infant Formula, Similac® Advance® Infant Formula with Iron, Similac® NeoSure® Advance® Infant Formula With Iron, Similac Natural Care Advance Low-Iron Human Milk Fortifier Ready To Use, all commercially available from Abbott Nutrition (Columbus, Ohio). The various PUFAs of the present disclosure can be substituted and/or added to the infant formulae described herein and to other infant formulae known to those in the art.

Nutritional Formulations: Examples of nutritional formulations include, but are not limited to, ENSURE®, ENSURE® HIGH PROTEIN, ENSURE PLUS®, ENSURE® POWDER, ENSURE® PUDDING, ENSURE® WITH FIBER, Oxepa™ Nutritional Product, all commercially available from Abbott Nutrition (Columbus, Ohio). The various nutritional supplements described above and known to others of skill in the art can be substituted and/or supplemented with the PUFAs produced in accordance with the present disclosure.

Pharmaceutical Compositions

The present disclosure also encompasses a pharmaceutical composition comprising one or more of the acids and/or resulting oils produced using the Δ9-elongase genes described herein, in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art. For example, PUFAs produced in accordance with the present disclosure can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present disclosure or derivatives thereof may be incorporated into commercial formulations such as Intralipids™. The typical normal adult plasma fatty acid profile comprises 6.64 to 9.46% ARA, 1.45 to 3.11% of DGLA, and 0.02 to 0.08% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present disclosure include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as weight of the patient, age of the patient, immune status of the patient, etc.

With respect to form, the composition may be, for example, a solution, a dispersion, a suspension, an emulsion or a sterile powder which is then reconstituted.

The present disclosure also includes the treatment of various disorders by use of the pharmaceutical and/or nutritional compositions described herein. In particular, the compositions of the present disclosure may be used to treat restenosis after angioplasty. Furthermore, symptoms of inflammation, rheumatoid arthritis, asthma and psoriasis may also be treated with the compositions of the disclosure. Evidence also indicates that PUFAs may be involved in calcium metabolism; thus, the compositions of the present disclosure may, perhaps, be utilized in the treatment or prevention of osteoporosis and of kidney or urinary tract stones.

Additionally, the compositions of the present disclosure may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present disclosure may also be useful for treating cachexia associated with cancer.

The compositions of the present disclosure may also be used to treat diabetes (see U.S. Pat. No. 4,826,877 and Horrobin et al., *Am. J. Clin. Nutr.* 1993) Vol. 57 (Suppl.) 732S-737S). Altered fatty acid metabolism and composition have been demonstrated in diabetic animals.

Furthermore, the compositions of the present disclosure, comprising PUFAs produced either directly or indirectly through the use of the Δ9-elongase enzyme, may also be used in the treatment of eczema, in the reduction of blood pressure, and in the improvement of mathematics examination scores. Additionally, the compositions of the present disclosure may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* (1976) Vol. 83, p. 85-101), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present disclosure include use in the treatment of AIDS, multiple sclerosis, and inflammatory skin disorders, as well as for maintenance of general health.

Additionally, the composition of the present disclosure may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present disclosure may be utilized in animal or aquaculture feed supplements, animal feed substitutes, animal vitamins or in animal topical ointments.

The present disclosure may be illustrated using the following non-limiting examples.

EXAMPLE 1 cDNA Library Construction from *Euglena deses Ehr.* CCMP 2916 and Sequence Analysis to Isolate Putative Δ9 Elongase Candidates Analysis of the fatty acid composition of some marine algae revealed the presence of a considerable amount of docosahexaenoic acid (DHA, 22:6 n-3) (15% by weight of total lipids) in *Euglena deses Ehr.* CCMP 2916 (see Table 1). In addition, this organism displayed intermediates of the alternate Δ8-desaturase/Δ9-elongase pathway (see FIG. 1), indicating that this pathway is active in this organism. Thus, it is predicted that this organism would contain an active Δ9-elongase capable of converting linoleic acid (LA, 18:2 n-6) to ω6-Eicosadienoic acid (ω6-EDA, 20:2 n-6), or α-linolenic acid (ALA, 18:3, n-3) to ω3-Eicosatrienoic acid (ω3-ETrA, 20:3n-3), as well as an active Δ8-desaturase that would convert ω6-Eicosadienoic acid (ω6-EDA, 20:2 n-6) to Dihomo-γ-linolenic acid (DGLA, 20:3 n-6), or ω3-Eicosatrienoic acid (ω3-EtrA, 20:3n-3) to ω3-Eicosatetraenoic acid (ω3-ETA, 20:4n-3) (see FIG. 1).

TABLE 1

Fatty acid profile of *Euglena* deses Ehr. CCMP 2916

| Fatty Acid | | % Total Lipid |
|---|---|---|
| Sterarie Acid | 18:0 | 0.529 |
| Oleic Acid | 18:1 n-9 | 1.663 |
| Linoleic Acid (LA) | 18:2 n-6 | 3.137 |
| γ Linolenic Acid (GLA) | 18:3 n-6 | 0.096 |
| α-Linolenic Acid (ALA) | 18:3 n-3 | 16.515 |
| Stearidonic Acid (SDA) | 18:4 n-3 | 0.126 |
| ω6-Eicosadienoic Acid (EDA) | 20:2 n-6 | 4.149 |
| Dihomo-γ-linoleic acid (DGLA) | 20:3 n-6 | 0.442 |
| Arachidonic Acid (ARA) | 20:4 n-6 | 3.719 |
| ω3-Eicosatrienoic acid (ω3-ETrA) | 20:3 n-3 | 1.984 |
| ω3-Eicosatetraenoic Acid (ω3-ETA) | 20:4 n-3 | 0.496 |
| Eicosapentaenoic acid (EPA) | 20:5 n-3 | 7.104 |
| Adrenic Acid (ADA) | 22:4 n-6 | 0.841 |
| ω6-Docosapentaenoic acid (ω6-DPA) | 22:5 n-6 | 5.775 |
| ω3-Docosapentaenoic acid (ω3-DPA) | 22:5 n-3 | 1.176 |
| Docosahexaenoic Acid (DHA) | 22:6 n-3 | 15.239 |

The goal of this study was to isolate the full-length Δ9-elongase gene from *Euglena deses Ehr.* CCMP 2916 and to characterize its enzymatic activity by expression in a heterologous host, *Saccharomyces cerevisiae.*

To isolate full-length genes from *Euglena deses Ehr.* CCMP 2916, a micro-cDNA library was constructed using total RNA isolated from the organism. For this, cell pellets of the *Euglena deses Ehr.* CCMP 2916 were obtained from Provasoli-Guillard-National Center for Marine Phytoplankton (CCMP-Bigelow Laboratories, West Boothbay, Me.), and total RNA was isolated from it using the Qiagen RNeasy Maxi kit (Qiagen, Valencia, Calif.) as per manufacturer's protocol. Briefly, frozen cell pellets were crushed in liquid nitrogen using a mortar and pestle, suspended in RLT buffer (Qiagen RNeasy Plant Mini kit), and passed through a QiaShredder. The RNA was purified using RNeasy maxi columns as per manufacturer's protocol.

The micro-cDNA library was constructed by Agencourt Biosciences (Waltham, Mass.), using 50 µg of RNA from *Euglena deses Ehr.* CCMP 2916 by proprietary technology. Agencourt uses several unique and proprietary steps during first strand that ultimately yields a 25 to 30% increased efficiency over commonly used techniques. During the proprietary process, the RNA is reverse transcribed into ssDNA using conditions designed to reduce or eliminate internal priming events. The combination of this and a specialized cycling program increases the number of full-length clones. Following second strand synthesis, the cDNA clones are then size selected at greater than 1.2 kb to decrease preferential cloning of small, truncated cDNAs. For the large insert library, the insert size selected is >4 kb to enhance for the larger insert clones. Following size selection, cDNA ends are polished and the cDNAs are digested using the rare cutting enzyme. A "rare-cutter" restriction enzyme, the site for which is introduced into the clones during the cDNA priming step, is then used to prepare the clones for directional cloning into the pAGEN vector. The "rare-cutter" restriction enzyme is 20 times less likely to cut within the cDNA clones, thus yielding many more full-length clones versus other cDNA library construction processes, which utilize more common restriction enzymes that cut at random intervals along the clone. The result is an insert with a 5' blunt end and a 3' overhang created from the rare cutting restriction enzyme. Because of this process, no additional adapter ligation is required to ensure directional cloning. This improves the overall efficiency of the cloning process. The vector is specially engineered for directional cloning without the use of 5' adaptors, further enhancing the transformation efficiency due to a reduced number of manipulations of the cDNA during cloning. After the primary cDNA library is complete, it is tested for the number of independent clones, the percentage of recombinant clones and the average insert size.

The clones are then transformed into DH10B *E. coli* (T1 phage resistant bacterial cells). The titer of the resulting library was $3.2 \times 10^6$ cfu/ml, with $3.52 \times 10^7$ number of independent colonies with an average insert size of 1.3 kb.

4224 clones from this cDNA library were sequenced, and vector-trimmed sequences were analyzed using BLAST to identify sequences with homology to known Δ9-elongase sequences. BLAST analysis revealed five putative hits from the *Euglena deses Ehr.* CCMP 2916 cDNA library with homology to known Δ9-elongase sequences from *Pavlova salina* (Accession #AAY15135; SEQ ID NO: 1; FIG. 4A), *Isochrysis galbana* (Accession #AF390174; SEQ ID NO: 2; FIG. 4B), *Eutreptiella* sp. (see WO 2007/061845 Δ2; SEQ ID NO: 3; FIG. 4C), *Euglena gracialis* (Accession #CAT16687; SEQ ID NO: 4; FIG. 4D), and *Euglena anabena* (see WO 2008/0194685 Δ1; SEQ ID NO: 5; FIG. 4E).

One EST clone designated 'plate2_MO7' (SEQ ID NO: 6; FIG. 5A), obtained from sequencing clones from the *Euglena deses Ehr.* CCMP 2916 cDNA library, showed high sequence homology to previously identified Δ9-elongases. This DNA fragment was 744 by in length, and its deduced amino acid sequence (SEQ ID NO: 7; FIG. 5B) displayed highest sequence identity (66% amino acid sequence identity) with the Δ9-elongase from *Euglena gracialis* (SEQ ID NO: 4). The plate2_MO7 gene fragment appeared to contain the 'ATG' start site of the gene based upon alignment with other Δ9-elongases, but did not contain the 3'-end of the putative *Euglena deses Ehr.* CCMP 2916 Δ9-elongase.

EXAMPLE 2

Isolation of the 3'-end of the plate2 MO7 Elongase from *Euglena deses Ehr.* CCMP 2916

The plate2_MO7 clone sequence from Example 1 was used as a template to isolate its 3'-end.

First strand cDNA was synthesized using the SMART™ RACE kit (BD Biosciences) according to the manufacturer's instructions. For synthesis of 3' RACE-ready cDNA, 1.5 µg total RNA from *Euglena deses Ehr*. CCMP 2916 and 1 µl of 3' CDS primer (5'-AAGCAGTGGTATCAACGCAGAGTAC (T)₃₀VN-3', wherein N=A, C, G, or T; and V=A, G, or C (SEQ ID NO: 8)) (12 µM) were mixed in a total volume of 5 µl in a nuclease-free PCR tube, incubated at 70° C. for 2 minutes, and snap-chilled on ice. After brief centrifugation, 2 µl of 5× first strand buffer [250 mM Tris-HCl (pH-8.3), 375 mM KCl and 30 mm MgCl₂], 1 µl of 0.1 M DTT and 1 µl of 10 mM dNTP mix was added to the tubes. After incubation at 42° C. for 2 minutes, 1 µl of reverse transcriptase (PowerScript™ RT, BD Biosciences) was added to the tube and incubated at 42° C. for 90 minutes. The first strand cDNA was diluted in 100 µl of Tricine-EDTA buffer [10 mM Tricine-KOH (pH 8.5), 1.0 mM EDTA] and enzymes heat inactivated at 72° C. for 7 minutes.

To isolate the 3'-end of the *Euglenoid* sp. *elongase* gene fragment (i.e., the plate2_MO7 clone sequence), primers were designed based on the sequence information from the partial gene sequence of plate2_MO7. Primary PCR amplification was carried out using the 3'-RACE ready cDNA as a template and the following primers: Eug Elo MO-7 FP1 (gene specific primer) (5'-AGG CGC TGT GGA TCT TCG TCT TCC-3') (SEQ ID NO: 9), in combination with RACE primer Universal Primer Mix A (UPM, BD Biosciences):

```
Long primer (0.4 µM):
                                    (SEQ ID NO: 10)
5'-CTA ATA CGA CTC ACT ATA GCA AGC AGT GGT ATC
AAC GCA GAG T-3';
and Short primer (2 µM):
                                    (SEQ ID NO: 11)
5'-CTA ATA CGA CTC ACT ATA GGG C-3'.
```

Amplification was carried out using 0.25 µl (100 mM) of the gene specific primer, 0.25 µl (100 mM) of the UPM primer, 2.5 µl of cDNA template, 2.5 µl of 2.5 mM dNTP, 5 µl of 5×PCR Buffer (Advantage® GC II polymerase buffer (Clontech), 200 mM Tricine-KOH (pH 9.2), 75 mM potassium acetate, 17.5 mM magnesium acetate, 25% DMSO, 18.75 µg/ml BSA, 0.005% Tween 20, 0.005% Nonidet-P40), 2.5 µl GC Melt Reagent (Clontech), 0.5 µl of 50× Advantage® GC I polymerase (Clontech), and 11.5 µL Milli-Q® water (Millipore), in a final reaction volume of 25 µl. Samples were denatured initially at 94° C. for 3 minutes, followed by 2 cycles of 94° C. for 30 seconds, 64° C. for 30 seconds, and 68° C. for 1.3 minutes; 3 cycles of 94° C. for 30 seconds, 62° C. for 30 seconds, and 68° C. for 1.30 minutes; 4 cycles of 94° C. for 30 seconds, 60° C. for 30 seconds, and 68° C. for 1.30 minutes; and 26 cycles of 94° C. for 30 seconds, 58° C. for 30 seconds, and 68° C. for 1.30 minutes. A final extension cycle at 68° C. for 10 minutes was carried out before the reaction was terminated at 4° C.

Analysis of the PCR products revealed very faint bands, which were likely due to low levels of the elongase gene transcripts in the cell. Hence, a nested PCR reaction was carried out using 1 µl of the product from the above-described primary PCR reaction as a template. Primers used for the nested PCR were Eug Elo MO-7 FP2 (a gene-specific primer): 5'-TCC CCG TGC CGA AGT CGT TCA TCA CC-3' (SEQ ID NO: 12), and the Universal Primer Mix A (UPM) primers (SEQ ID NOs: 10 and 11). PCR reaction conditions and cycling parameters were same as used for the primary PCR reaction.

A 548 by amplicon (SEQ ID NO: 13; FIG. 6A), obtained by nested PCR, was gel purified using the Qiagen Gel Purification kit (Qiagen), and was cloned into pTZ57R/T vector (T/A cloning vector, MBI Fermentas) and sequenced. Sequencing revealed that this fragment (SEQ ID NO: 13) was contained the complete 3'-end of the plate2_MO7 elongase fragment along with the 'TAG' stop codon and downstream region containing the polyA tail. The predicted amino acid sequence of this fragment (SEQ ID NOs: 14 and 30-32) is shown in FIG. 6B. The first asterisk denotes the stop site of the plate 2_MO7 encoded protein.

EXAMPLE 3

Isolation of the Full-Length plate2 M07 Elongase Gene from *Euglena deses Ehr*. CCMP 2916

The full-length gene sequence of plate2_MO7 elongase was isolated by PCR amplification using the *Euglena deses Ehr*. cDNA library as the template, and primers that were designed to contain the 5'- and 3'-ends of the plate2_M07 gene based upon sequence information obtained in Example 1 and Example 2. In addition, BamHI/HindIII sites were incorporated into the primers (underlined) to facilitate cloning of the gene into the BamHI/HindIII sites of the yeast expression vector, pYX242. The following primer sequences were used:

```
M07-Elo forward primer:
                                    (SEQ ID NO: 15)
5'-CAC CAT GGA TCC ATG GAC GTC GCG ACT ACG CTG
G-3',
and M07-Elo reverse primer:
                                    (SEQ ID NO: 16)
5'-ACG CGT AAG CTT CTA GTC CAC TTT CTT CTC ATC
CTT C-3'.
```

Amplification was carried out using 0.5 µl (100 µM) of each primer, 1 µl (~110 ng) of the *Euglena deses Ehr*. cDNA library plasmid pool as the template, 5 µl of 2.5 mM dNTP, 10 µl of 5× Phusion GC Buffer (Finnzymes), 5 µL of DMSO, 0.5 µL (1 U) of Phusion polymerase (Finnzymes), and 27.5 µL of Milli-Q® water (Millipore). Samples were denatured initially at 98° C. for 3 minutes, followed by 2 cycles of 98° C. for 8 seconds, 60° C. for 12 seconds, and 72° C. for 45 seconds; and 28 cycles of 98° C. for 8 seconds, 58° C. for 12 seconds, and 72° C. for 45 seconds. A final extension cycle at 72° C. for 3 minutes was carried out before the reaction was terminated at 4° C.

PCR resulted in an ~789 bp product, which was cloned into the Bam HI/Hind III sites of pYX242 vector and transformed into *E. coli* DH5α (Invitrogen). Plasmid DNA thus obtained was sequenced to obtain the full-length gene sequence of the 789 bp gene, designated "Eug-M07-ELO#10' (SEQ ID NO: 17; FIG. 7A). SEQ ID NO: 17 was deposited with the American Type Culture Collection, 10801 University Boulevard, Manassas, Va. 20110-2209, on Jul. 10, 2009, under the terms of the Budapest Treaty, and was accorded ATCC deposit number PTA-10200. This gene was thought to encode the putative Δ9-elongase from *Euglena deses Ehr*. CCMP 2916, with a predicted length of 262 amino acids (SEQ ID NO: 18; FIG. 7B). This gene was used for expression studies to characterize its enzymatic activity.

Figure 2A:
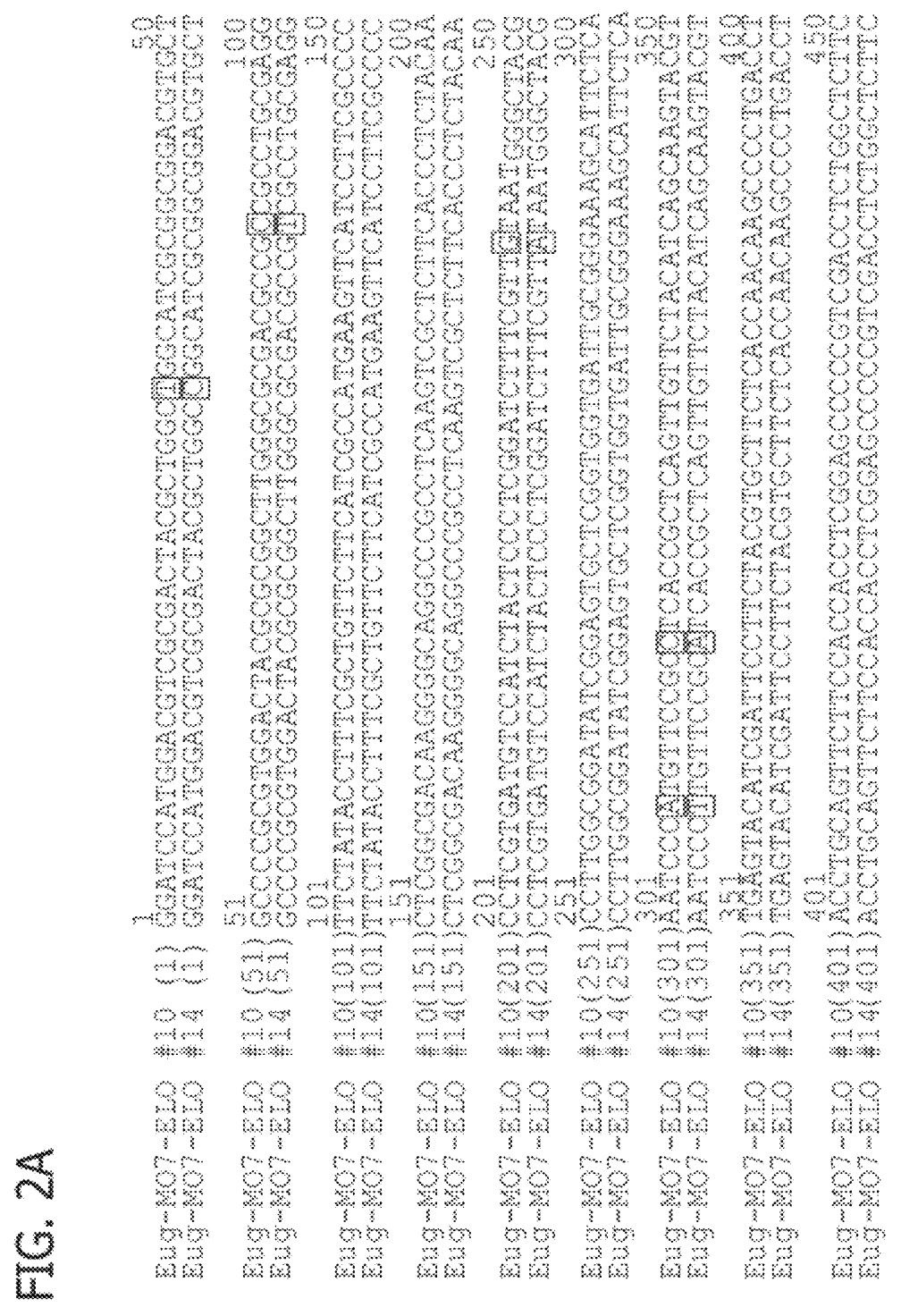

In addition to the Eug-M07-ELO#10 clone, additional variant clones were identified during sequencing that displayed some sequence variations in certain regions across the full-length gene. These sequence variations probably arose during the process of PCR amplification. Sequence analysis of one such variant, Eug-M07-ELO #14 revealed a number of nucleotide and corresponding amino acid changes when compared to the original Eug-M07-ELO#10 clone (see Table 2 and FIGS. 2A and 2B). The nucleotide (SEQ ID NO: 19) and predicted amino acid sequence (SEQ ID NO: 20) of Eug-M07-ELO #14 are shown in FIGS. 8A and 8B, respectively. Both the original Eug-M07-ELO#10 clone and the variant Eug-M07-ELO #14 were used for expression analysis.

TABLE 2

Nucleotide and amino acid changes in the variant clone Eug-MO7-ELO#14 in comparison to the original clone Eug-MO7-ELO#10

| Nucleotide Changes<br>Eug-MO7-ELO#10 (SEQ ID NO: 17) ⇒<br>Eug-MO7-ELO#14 (SEQ ID NO: 19) | Corresponding Amino Acid<br>Changes (SEQ ID NO: 18<br>18 ⇒ SEQ ID NO: 20) |
|---|---|
| $GCT_{24} \Rightarrow GCC_{24}$ | Silent mutation |
| $GC_{83}C \Rightarrow GT_{83}C$ | $A_{28} \Rightarrow V_{28}$ |
| $G_{232}TA \Rightarrow A_{232}TA$ | $V_{78} \Rightarrow I_{78}$ |
| $A_{301}TG \Rightarrow T_{301}TG$ | $M_{101} \Rightarrow L_{101}$ |
| $C_{310}TC \Rightarrow A_{310}TC$ | $L_{104} \Rightarrow I_{104}$ |
| $ACA_{630} \Rightarrow ACT_{630}$ | Silent mutation |
| $AAA_{750} \Rightarrow AAG_{750}$ | Silent mutation |

Blast searches, using Eug-M07-ELO #10 as query, for similarity to sequences contained in the BLAST 'nr' database revealed that the predicted amino acid sequence encoded by Eug-M07-ELO#10 (SEQ ID NO: 18) displayed highest amino acid sequence identity (36% sequence identity) with the *Isochrysis galbana* Δ9-elongase (SEQ ID NO: 2). Pair wise alignment of SEQ ID NO: 18 to the known Δ9-elongase from *Euglena gracialis* (Accession #CAT 16687; SEQ ID NO: 4) revealed a much higher amino acid sequence identity (66% identity). Here the default parameters of Vector NTI®AlignX program were used for pair wise alignment. Pair wise alignment with the *Pavlova salina* Δ9-elongase (SEQ ID NO: 1) revealed only ~15% sequence identity.

Unlike desaturases, the elongase enzymes display very few highly conserved motifs. These enzymes are highly hydrophobic proteins containing four to five hydrophobic stretches that are predicted to be membrane-spanning region. In addition a highly conserved histidine box (HXXHH) (SEQ ID NO: 28) is found embedded in the fourth membrane spanning region and is essential for enzymatic activity (see Leonard, et al., "Elongation of long-chain fatty acids," *Prog Lipid Res.* (2004) Vol. 43, p. 36-54). In some elongases, the first histidine residue of the 'HXXHH' motif (SEQ ID NO: 28) is replaced with a Glutamine (Q) resulting in 'QXXHH' (SEQ ID NO: 29) as the conserved motif. This QXXHH (SEQ ID NO: 29) motif is found in most of the Δ9-elongases including Eug-M07-ELO#10. In addition, the Eug-M07-ELO#10 elongase contains other invariant residues that are present in most elongases to date, as described by Leonard, et al., "Elongation of long-chain fatty acids," *Prog Lipid Res.* (2004) Vol. 43, p. 36-54.

FIGS. 3A and 3B depict an alignment of the amino acid sequence from Eug-M07-ELO#10 elongase with other known elongases that have varying substrate specificity. These include the Mouse Elovl4 elongase (Accession # AAG47667; SEQ ID NO: 21; FIG. 9A), human ELOVL2 elongase (Acession # NP_060240; SEQ ID NO: 22; FIG. 9B), and *C. elegans* elongase (Accession # AF244356; SEQ ID NO: 23), in addition to the Δ9-elongases from *Euglena gracialis* (SEQ ID NO: 4) and *Isochrysis galbana* (SEQ ID NO: 2). A box is drawn around invariant amino acids in the alignment. It is assumed that these invariant residues are important determinants for functionality of these elongating enzymes due to high degree of conservation across species.

Alignment was carried out using Vector NTI software that uses a modified ClustalW algorithm.

EXAMPLE 4

Characterization of the Enzymatic Activity of the Putative Δ9-Elongase Encoded by the Gene Eug-MO7-ELO#10

The Eug-M07-ELO#10 and Eug-M07-ELO#14 variant encoding a putative Δ9-elongase were cloned into BamHI/HindIII sites of the yeast expression vector, pYX242 (Novagen), respectively. These constructs were transformed into competent *Saccharomyces cerevisiae* strain SC334 cells. Yeast transformation was carried out using the Alkali-Cation Yeast Transformation Kit (QBioGene) according to conditions specified by the manufacturer. Transformants were selected for leucine auxotrophy on media lacking leucine (DOB [-Leu]).

To characterize the elongase activity of the enzymes encoded by Eug-M07-ELO#10 and Eug-M07-ELO#14, transformants were grown in the presence of 50 μM specific fatty acid substrates (listed below) and conversion to specific product was used to determine substrate specificity:

For Δ9-Elongase Activity:

Linoleic acid (18:2 n-6)⇒Eicosadienoic acid (EDA, 20:2 n-6)

Alpha-linolenic acid (18:3 n-3)⇒Eicosatrienoic acid (ETrA, 20:3 n-3)

For $C_{18}$-elongase

Gamma-linolenic acid (GLA, 18:3 n-6)⇒Dihomo-γ-linolenic acid (DGLA, 20:3 n-6)

Stearidonic Acid (SDA, 18:4 N-3)⇒ω3-Eicoastetraenoic Acid (ω3-ETA, 20:4 n-3)

For $C_{20}$-elongase activity:

Arachidonic acid (ARA, 20:4 n-6)⇒Adrenic acid (ω6-ADA, 22:4 n-6)

Eicosapentaenoic acid (EPA, 20:5 n-3)⇒ω3-Docosapentaenoic acid (ω3-DPA, 22:5 n-3)

The negative control strain consisted of pYX242 vector expressed in *S. cerevisiae* 334.

The transformed colonies isolated from selective DOB [-Leu] media were grown overnight in 10 ml of YPD liquid broth at 30° C., with vigorous agitation. 5 ml of this overnight culture was then added to 45 ml of selective media (DOB [-Leu]) containing 50 μM (final concentration) of various fatty acid substrates (as specified), and these were vigorously agitated (250 rpm) for 48 to 72 hours (as indicated) at 24° C.

For total lipid extraction, yeast cells were spun down at 2000 rpm for 15 minutes and 0.5 ml water was added, samples vortexed, followed by addition of 10 ml methanol with gentle swirling. 20 ml chloroform was then added, samples were vortexed for 1 minute at high speed and allowed to stand for 2 hours at room temperature. 6 ml saline was then added to the sample followed by centrifugation at 2200 rpm for 10 minutes. The upper chloroform layer was removed to a clean/dry 30 ml vial and chloroform evaporated to dryness at 40° C. under a stream of nitrogen. Once the solvents had completely evaporated, 2 ml chloroform was added to each vial and samples were derivatized.

For derivitization of lipids to Fatty acid methyl esters (FAME), each tube was spiked with 100 μl internal standard (17.216 μg/100 μl) Triheptadecanoin. Chloroform was evaporated to dryness under nitrogen at 40° C., 2 ml Boron Trifluoride in 14% Methanol was added, followed by addition of 2 drops (~50 μl) Toluene. Each vial was flushed with nitrogen, and heated for 15 minutes at 95° C. After vials had cooled, 2 ml saline was added and lipids extracted with 4 ml hexane by vigorously vortexing for 1 minute. The hexane extract was then transferred into a 20 ml clean/dry screw-cap tube, 5 ml di-H$_2$O was added and sample vortexed, and centrifuged at 1500 rpm for 4 minutes. The washed hexane was then transferred into a 20 ml reagent tube. Hexane was evaporated to dryness and each sample reconstituted with 0.5 ml fresh hexane. The reconstituted final hexane was vortexed to disperse the lipids. The entire sample was then loaded into the GC auto sampler vials and 4 μl was injected for analysis. The GC was calibrated with the NuChek Std. 461.

The percent conversion of substrate to product was calculated using the formula:

$$\frac{[\text{product}]}{[\text{product}] + [\text{substrate}]} \times 100$$

Table 3 represents the enzyme activity of the Eug-M07-ELO#10- and Eug-M07-ELO#14 encoded proteins based on the percent conversion of substrate added. Eug-M07-ELO#10 encoded protein converted 10.5% of LA (18:2n-6) to EDA (20:2 n-6), and 23.2% of ALA (18:3n-3) to ETrA (20:3n-3). This indicated that the Eug-M07-ELO#10 gene encodes a Δ9-elongase that can recognize both n-6 and n-3 fatty acid substrates. The variant clone, Eug-M07-ELO#14 encoded protein also displayed 49 elongase activity, converting converted 7.84% of LA (18:2n-6) to EDA (20:2 n-6), and 17.15% of ALA (18:3n-3) to ETrA (20:3n-3). However this activity was lower that that of the original Eug-M07-ELO#10 encoded protein. This indicates that the residues that differ between Eug-M07-ELO#14 and Eug-M07-ELO#10 are important determinants of 49-elongating activity of this enzyme.

Very low background (non-specific conversion of substrate) activity was detected with the vector-only control (see Table 3). Both Eug-M07-ELO#10 & Eug-M07-ELO#14 encoded enzymes did not have activity on any of the other PUFA substrates tested (see Table 4), indicating that this enzyme is specific for substrates involved in the alternate Δ8-desaturase/Δ9-elongase pathway (see FIG. 1).

TABLE 3

Δ9-elongase activity of Eug-MO7-ELO#10 and Eug-MO7-ELO#14 encoded proteins expressed in *Saccharomyces cerevisiae* strain SC334

| % Total Fatty Acid | Eug-M07-ELO#10 | Eug-M07-ELO#14 | Vector Control |
|---|---|---|---|
| LA (18:2 n-6)$^a$ | 8.84 | 12.575 | 10.65 |
| EDA (20:2n-6, Δ11, 14)$^b$ | 1.038 | 1.066 | 0.0985 |
| % LA → EDA Conversion$^c$ | 10.5 | 7.84 | 0.91 |
| ALA (18:3 n-3)$^a$ | 8.788 | 10.89 | 13.96 |
| ETrA (20:3 n-3, Δ11, 14, 17)$^b$ | 2.665 | 2.198 | 0.166 |
| % ALA → ETrA Conversion$^c$ | 23.2 | 17.15 | 1.22 |

$^a$Cultures grown in presence of 50 μM substrate at 24° C. for 48 hours. Numbers represent an average of 2 different experiments.
$^b$Amount of product formed
$^c$% Conversion = ([product]/{[product] + [substrate]}) × 100

TABLE 4

Specificity of Elongase Activity of Eug-MO7-ELO#10 & Eug-MO7-ELO#14 encoded proteins expressed in *Saccharomyces cerevisiae* strain SC334

| % Total Fatty Acid | Eug-MO7-ELO#10 | Eug-MO7-ELO#14 | Vector Control |
|---|---|---|---|
| GLA (18:3 n-6)$^a$ | 12.90 | 14.23 | 14.49 |
| DGLA (20:3n-6)$^b$ | 0.171 | 0.194 | 0.164 |
| % GLA → DGLA Conversion$^c$ | 1.31 | 1.34 | 1.12 |
| ARA (20:4 n-6)$^a$ | 27.645 | 25.044 | 22.711 |
| Adrenic Acid (22:4 n-6)$^b$ | 0.0 | 0.0 | 0.019 |
| % ARA → Adrenic Acid Conversion$^c$ | 0 | 0 | 0.08 |
| SDA (18:4 n-3)$^a$ | 6.899 | 8.335 | 8.642 |
| ω3-ETA (20:4n-3)$^b$ | 0.077 | 0.047 | 0.198 |
| % SDA → ω3-ETA Conversion$^c$ | 1.10 | 0.56 | 2.24 |
| EPA (20:5 n-3)$^a$ | 18.84 | 13.351 | 12.016 |
| ω3-DPA (22:5 n-3)$^b$ | 0.131 | 0.093 | 0.083 |
| % EPA → ω3-DPA Conversion$^c$ | 0.69 | 0.69 | 0.69 |

$^a$Cultures grown in presence of 50 μM substrate at 24° C. for 48 hours. Numbers represent an average of 2 different experiments.
$^b$Amount of product formed
$^c$% Conversion = ([product]/{[product] + [substrate]}) × 100

EXAMPLE 5

Expression of the Δ9-Elongase 'Eug-M07-ELO#10' in Plant Seeds

The coding sequence of the Eug-M07-ELO#10 elongase was amplified by PCR from a plasmid containing the corresponding gene with the following sense and antisense oligonucleotide primers (added restriction enzyme sites are underlined):

```
                                          (SEQ ID NO: 24)
5'-TATAGAATTCAAATGGACGTCGCGACTACGCTG-3',
and (SEQ ID NO: 25)
5'-TATTCTCGAGTTCTAGTCCACTTTCTTCTCATCCTTC-3'.
```

The PCR reaction was conducted with high-fidelity Phusion polymerase (New England Biolabs). The PCR amplified gene was digested with restriction enzymes EcoRI and XhoI, and the resulting product was linked on its 5'-end to the seed-specific glycinin-1 promoter from soybean and on its 3'-end to the glycinin-1 3' untranslated region in the binary vector p0308-DsRed to generate the plasmid 'pEugELO'. The glycinin-1 regulatory elements have been previously described by Nielsen, et al., "Characterization of the glycinin gene family in soybean," *Plant Cell* (1989) Vol. 1, p. 313-328. This vector also contains a Ds-Red transgene under control of the cassava mosaic virus promoter for selection of transformed seeds by fluorescence and a kanamycin resistance marker for bacterial selection. As a control for these experiments, the *Isochrysis galbana* Δ9-elongase gene (SEQ ID NO: 2) was also cloned as an EcoRI/XhoI fragment under control of the glycinin-1 promoter in p0308-Ds-Red to generate the plasmid 'pIsoD9'.

pEugELO and pIsoD9 were introduced into *Agrobacterium tumefaciens* strain C58MP90 by electroporation. Kanamycin-resistant *agrobacterium* was then used for transformation of *Arabidopsis thaliana* ecotype Col-0 by the floral dip method (Clough, et al., "Floral dip: a simplified method for *Agrobacterium*-mediated transformation of *Arabidopsis* thaliana," *Plant J*, (1998) Vol. 16, p. 735-743). Following the *agrobacterium* floral dip, plants were maintained at 22° C. with 16 hour day length until reaching maturity and dry down. For these experiments, a fad3/fae1 mutant of *Arabidopsis* was used that contains low levels of α-linolenic acid and very-long chain fatty acids (>C20) but elevated levels of linoleic acid in its seed oil (Cahoon, et al., "Conjugated fatty acids accumulate to high levels in phospholipids of metabolically engineered soybean and *Arabidopsis* seeds," *Phytochemistry* (2006) Vol. 67, p. 1166-1176). This genetic background approximates the fatty acid profile of seed oils from crops such as safflower and low linolenic acid soybean. Transgenic seeds obtained from the *agrobacterium*-dipped *Arabidopsis* plants were identified by fluorescence of the DsRed marker protein using the methodology described by Pidkowich, et al., "Modulating seed beta-ketoacyl-acyl carrier protein synthase II level converts the composition of a temperate seed oil to that of a palm-like tropical oil," *Proc Natl Acad Sci USA* (2007) Vol. 104, p. 4742-4747. Single transgenic and non-transgenic control seeds were subjected to direct transesterification of the constituent lipids, including triacylglycerols, by use of trimethylsulfonium hydroxide (TMSH) reagent as described by Cahoon and Shanklin, "Substrate-dependent mutant complementation to select fatty acid desaturase variants for metabolic engineering of plant seed oils," *Proc Natl Acad Sci USA* (2000) Vol. 97, p. 12350-12355. Fatty acid methyl esters obtained from the single seeds were analyzed by gas chromatography with flame ionization detection by use of an Agilent 6890 gas chromatograph fitted with an INNOWax column (30 m length×0.25 mm inner diameter) and oven temperature programming from 185° C. (1 minute hold) to 230° C. (2 minute hold) at 7° C./minute. Component fatty acid methyl esters were identified based on their retention times relative to fatty acid methyl esters of known identity from seeds of wild-type *Arabidopsis thaliana* Col-0 and by comparison of retention times with those of standard fatty acid methyl esters.

Shown in Table 5 are the fatty acid compositions of single T1 seeds from six independent transformation events from plants transformed with pEugELO construct. Also shown are the fatty acid compositions of single T1 seeds representing independent events from plants transformed with pIsoD9 construct, the control 49 elongase (see Table 6). The major change in the fatty acid composition of transgenic seeds from the pEugELO transformation relative to non-transformed fad3/fae1 seeds (see Table 7) was the presence of high levels of EDA (20:2n-6, Δ11,14). In these seeds, relative amounts of 20:2 ranged from 40% to 49% (w/w) of the total fatty acids. By comparison 20:2 accounted for >0.5% of the total fatty acids of non-transgenic fad3/fae1 seeds (see Table 7). This was accompanied by concomitant decreases in relative amounts of LA (18:2n-6, Δ9, 12) from approximately 50% in non-transgenic fad3/fae1 seeds (see Table 7) to as low as 14% in the pEugELO. This is consistent with 18:2 serving as the primary substrate for 20:2 synthesis conferred by the Eug-M07-ELO#10 elongase. Amounts of Eicosenoic acid (20:1411) and Eicosanoic acid (20:0) were also elevated in the pEugELO-transformed seeds relative to non-transgenic fad3/fae1 seeds, but each of these fatty acids composed <3% of the total fatty acids in the transgenic seeds. These findings indicate that Eug-M07-ELO#10 elongase has substrate preference in plants for $C_{18}$ PUFAs such as LA (18:2n-6) and is an effective enzyme for the production of 20:2 in seeds that are enriched in LA (18:2n-6). For comparison, seeds engineered to express the *Isochrysis galbana* Δ9-ELO (pIsoD9) accumulated 20:2 to amounts of 30 to 40% of the total fatty acids and 20:0 and 20:1 each to amounts of <3% of the total fatty acids (see Table 6).

TABLE 5[a]

Fatty acid composition of single T1 transgenic *Arabidopsis* fad3/fae1 seeds expressing Eug-MO7-ELO#10.

| Fatty acid | Line 1 | Line 2 | Line 3 | Line 4 | Line 5 | Line 6 |
|---|---|---|---|---|---|---|
| 16:0 | 9.5 | 9.1 | 8.2 | 7.1 | 8.2 | 8.0 |
| 18:0 | 3.5 | 3.6 | 4.1 | 3.4 | 3.2 | 3.5 |
| 18:1 | 18.5 | 17.5 | 19.1 | 20.3 | 12.7 | 16.5 |
| 18:2 | 21.3 | 14.3 | 14.1 | 15.6 | 19.9 | 21.5 |
| 18:3 | 0.9 | 1.3 | >0.1 | >0.1 | >0.1 | 0.7 |
| 20:0 | 1.0 | 1.0 | 1.2 | 0.9 | 0.8 | 0.9 |
| 20:1 | 1.3 | 1.2 | 1.5 | 2.3 | 2.0 | 2.3 |
| 20:2 | 42.3 | 49.4 | 48.6 | 47.2 | 49.3 | 44.3 |
| other | 1.7 | 2.6 | 2.4 | 2.1 | 2.1 | 1.8 |

[a]Each seed represents an independent transgenic event. Values shown are the wt % of the total fatty acids in the seed.

TABLE 6[a]

Fatty acid composition of single $T_1$ transgenic *Arabidopsis* fad3/fae1 seeds expressing the Isochrysis galbana ELO.

| Fatty acid | Line 1 | Line 2 | Line 3 | Line 4 | Line 5 |
|---|---|---|---|---|---|
| 16:0 | 7.5 | 8.4 | 6.7 | 7.4 | 7.2 |
| 18:0 | 3.9 | 3.3 | 4.0 | 3.3 | 4.3 |
| 18:1 | 22.8 | 19.5 | 15.9 | 15.2 | 20.8 |
| 18:2 | 26.3 | 23.9 | 29.2 | 25.3 | 26.2 |
| 18:3 | 1.0 | 1.2 | 0.4 | 0.6 | 0.9 |
| 20:0 | 1.1 | 0.9 | 1.2 | 1.0 | 1.1 |
| 20:1 | 2.0 | 1.6 | 2.8 | 2.2 | 2.2 |
| 20:2 | 34.1 | 38.8 | 37.1 | 40.2 | 36.1 |
| other | 1.1 | 2.3 | 2.2 | 2.9 | 1.1 |

[a]Each seed represents an independent transgenic event. Values shown are the wt % of the total fatty acids in the seed.

TABLE 7[a]

Fatty acid composition of single *Arabidopsis* fad3/fae1 control seeds.

| Fatty acid | Line 1 | Line 2 | Line 3 | Line 4 | Line 5 |
|---|---|---|---|---|---|
| 16:0 | 7.9 | 8.4 | 6.9 | 8.9 | 8.0 |
| 18:0 | 4.9 | 3.9 | 3.2 | 5.3 | 3.8 |
| 18:1 | 28.6 | 34.7 | 40.6 | 32.5 | 31.1 |
| 18:2 | 53.3 | 49.6 | 46.8 | 50.9 | 53.6 |
| 18:3 | 2.6 | 1.8 | 1.0 | 1.3 | 1.5 |
| 20:0 | 1.3 | 0.7 | 0.8 | 1.0 | 0.8 |
| 20:1 | 0.9 | 0.4 | 0.4 | 0.2 | 0.5 |
| 20:2 | ≧0.1 | ≧0.1 | ≧0.1 | ≧0.1 | ≧0.1 |
| other | 0.1 | 0.2 | 0.1 | 0.1 | 0.5 |

[a]Values shown are the wt % of the total fatty acids in the seed.

EXAMPLE 6

Coexpression of the Δ9-Elongase Eug-MO7-ELO#10 with a Δ8-Desaturase

It is possible to co-express Eug-M07-ELO#10 along with a Δ8-desaturase to reconstruct the alternate Δ8-desaturase/Δ9-elongase pathway leading to ARA production. In addition it will be possible to coexpress three genes, the Δ9-elongase 'Eug-MO7-ELO#10' along with a Δ8-desaturase and a Δ5-desaturase in a heterologous host such as oilseed plants or oleaginous yeast to reconstruct the ARA biosynthesis pathway with will result in ARA production in these heterologous hosts.

In view of the above, it will be seen that the several objects of the disclosure are achieved and other advantageous results attained.

As various changes could be made in the above matter without departing from the scope of the disclosure, it is intended that all matter contained in the above description shall be interpreted as illustrative and not in a limiting sense.

---

What is claimed is:

1. An isolated nucleic acid molecule or fragment thereof comprising or complementary to a nucleotide sequence encoding a polypeptide having elongase activity, wherein the polypeptide comprises an amino acid sequence having at least 90% sequence identity to an amino acid sequence selected from the group consisting of SEQ ID NO: 18 and SEQ ID NO: 20.

2. An isolated nucleic acid molecule or fragment thereof comprising or complementary to a nucleotide sequence having at least 90% sequence identity to a nucleotide sequence selected from the group consisting of SEQ ID NO: 17 and SEQ ID NO: 19.

3. The isolated nucleic acid molecule of claim 1 or 2 wherein the nucleotide sequence encodes a functionally active elongase which utilizes a polyunsaturated fatty acid as a substrate.

4. The isolated nucleic acid molecule of claim 1 or 2 wherein the isolated nucleic acid molecule is from a *Euglenoid* sp.

5. The isolated nucleic acid molecule of claim 4 wherein the isolated nucleic acid molecule is from *Euglena deses Ehr*. CCMP 2916.

6. An expression vector comprising a nucleic acid molecule operably linked to a regulatory sequence, wherein the nucleic acid molecule comprises or is complementary to a nucleotide sequence having at least 90% sequence identity to a nucleotide sequence selected from the group consisting of SEQ ID NO: 17 and SEQ ID NO: 19.

7. A host cell comprising the expression vector of claim 6.

8. The host cell of claim 7 wherein the host cell is selected from the group consisting of a eukaryotic cell and a prokaryotic cell.

9. The host cell of claim 8 wherein the eukaryotic cell is selected from the group consisting of: a mammalian cell, an insect cell, a plant cell, and a fungal cell.

10. The host cell of claim 9 wherein the plant cell is from an oilseed plant selected from the group consisting of: soybean, *Brassica* species, safflower, sunflower, maize, cotton, and flax.

11. A plant cell, plant seed, plant, or plant tissue comprising the expression vector of claim 6, wherein expression of the nucleotide sequence of the expression vector results in production of at least one polyunsaturated fatty acid by the plant cell, plant seed, plant, or plant tissue.

12. The plant cell, plant seed, plant, or plant tissue of claim 11 wherein the polyunsaturated fatty acid is selected from the group consisting of ω6-eicosadienoic acid (ω6-EDA), ω3-eicosatrienoic acid (ω3-ETrA), and combinations thereof.

13. A method of producing a Δ9-elongase, the method comprising the steps of:
   a) isolating a nucleic acid molecule comprising or complementary to a nucleotide sequence having at least 90% sequence identity to a nucleotide sequence selected from the group consisting of: SEQ ID NO: 17 and SEQ ID NO: 19;
   b) constructing an expression vector comprising i) the isolated nucleotide sequence operably linked to ii) a regulatory sequence; and
   c) introducing the expression vector into a host cell for a time and under conditions sufficient for production of the Δ9-elongase.

14. The method of claim 13 wherein the host cell is selected from the group consisting of a eukaryotic cell and a prokaryotic cell.

15. The method of claim 14 wherein the eukaryotic cell is selected from the group consisting of a mammalian cell, an insect cell, a plant cell, and a fungal cell.

16. The method of claim 15 wherein the plant cell is from an oilseed plant selected from the group consisting of soybean, *Brassica species*, safflower, sunflower, maize, cotton, and flax.

17. A method for producing a polyunsaturated fatty acid comprising the steps of:
  a) isolating a nucleic acid molecule comprising or complementary to a nucleotide sequence having at least 90% sequence identity to a nucleotide sequence selected from the group consisting of SEQ ID NO: 17 and SEQ ID NO: 19;
  b) constructing an expression vector comprising i) the isolated nucleotide sequence operably linked to ii) a regulatory sequence;
  c) introducing the expression vector into a host cell for a time and under conditions sufficient for expression of a Δ9-elongase; and
  d) exposing the expressed Δ9-elongase to a substrate polyunsaturated fatty acid in order to convert the substrate polyunsaturated fatty acid to a first product polyunsaturated fatty acid.

18. The method of claim 17 wherein the substrate polyunsaturated fatty acid is linoleic acid (LA) and the first product polyunsaturated fatty acid is ω6-eicosadienoic acid (ω6-EDA).

19. The method of claim 17 wherein the substrate polyunsaturated fatty acid is α-linolenic acid (ALA) and the first product polyunsaturated fatty acid is ω3-eicosatrienoic acid (ω3-ETrA).

20. The method of claim 17 further comprising the step of exposing the first product polyunsaturated fatty acid to at least one desaturase, at least one additional elongase, or combinations thereof, in order to convert the first product polyunsaturated fatty acid to a second or subsequent product polyunsaturated fatty acid.

21. The method of claim 20 wherein the second or subsequent product polyunsaturated fatty acid is selected from the group consisting of dihomo-γ-linolenic acid (DGLA), ω3-eicosatetraenoic acid (ω3-ETA), arachidonic acid (ARA), eicosapentaenoic acid (EPA), docosapentaenoic acid (DPA), docosahexaenoic acid (DHA), and combinations thereof.

22. A method for producing a polyunsaturated fatty acid in a host cell comprising the steps of:
  a) isolating a nucleic acid molecule comprising or complementary to a nucleotide sequence having at least 90% sequence identity to a nucleotide sequence selected from the group consisting of SEQ ID NO: 17 and SEQ ID NO: 19;
  b) constructing an expression vector comprising i) the isolated nucleotide sequence operably linked to ii) a regulatory sequence;
  c) introducing i) the expression vector and ii) at least one additional recombinant DNA construct comprising an isolated nucleotide sequence encoding a Δ8-desaturase and operably linked to at least one regulatory sequence, into a host cell for a time and under conditions sufficient for expression of a Δ9-elongase and the Δ8-desaturase; and
  d) exposing the expressed Δ9-elongase and the Δ8-desaturase to a substrate polyunsaturated fatty acid selected from the group consisting of linoleic acid (LA), α-linolenic acid (ALA), and combinations thereof, in order to convert the substrate polyunsaturated fatty acid to a first product polyunsaturated fatty acid.

23. The method of claim 22 wherein the first product polyunsaturated fatty acid is selected from the group consisting of dihomo-γ-linolenic acid (DGLA), ω3-eicosatetraenoic acid (ω3-ETA), and combinations thereof.

24. The method of claim 22 further comprising the step of exposing the first product polyunsaturated fatty acid to at least one additional desaturase or to at least one additional elongase in order to convert the first product polyunsaturated fatty acid to a second or subsequent polyunsaturated fatty acid.

25. The method of claim 24 wherein the second or subsequent polyunsaturated fatty acid is selected from the group consisting of arachidonic acid (ARA), eicosapentaenoic acid (EPA), docosapentaenoic acid (DPA), docosahexaenoic acid (DHA), and combinations thereof.

26. The method of claim 22 wherein the host cell is selected from the group consisting of a prokaryotic cell and a eukaryotic cell.

27. The method of claim 26 wherein the eukaryotic cell is selected from the group consisting of a mammalian cell, an insect cell, a plant cell, and a fungal cell.

28. The method of claim 27 wherein the plant cell is from an oilseed plant selected from the group consisting of soybean, *Brassica species*, safflower, sunflower, maize, cotton, and flax.

29. The method of claim 22 further comprising introducing into the host cell a recombinant DNA construct comprising i) an isolated nucleotide sequence encoding a Δ5-desaturase operably linked to ii) a regulatory sequence.

30. A method for producing a transgenic plant comprising transforming a plant cell with at least one isolated nucleic acid molecule or fragment thereof of claim 2 and regenerating a transgenic plant from the transformed plant cell.

31. The method of claim 30 wherein the plant cell is from an oilseed plant selected from the group consisting of soybean, *Brassica species*, safflower, sunflower, maize, cotton, and flax.

32. A transgenic seed obtained from the transgenic plant made by the method of claim 30.

33. A transgenic seed comprising the expression vector of claim 6.

* * * * *

SEQUENCE LISTING

```
<160> NUMBER OF SEQ ID NOS: 32

<210> SEQ ID NO 1
<211> LENGTH: 302
<212> TYPE: PRT
<213> ORGANISM: Pavlova salina

<400> SEQUENCE: 1

Met Lys Ala Ala Ala Gly Lys Val Gln Gln Glu Ala Glu Arg Leu Thr
1               5                   10                  15

Ala Gly Leu Trp Leu Pro Met Met Leu Ala Ala Gly Tyr Leu Leu Val
            20                  25                  30

Leu Ser Ala Asn Arg Ala Ser Phe Tyr Glu Asn Ile Asn Asn Glu Lys
        35                  40                  45

Gly Ala Tyr Ser Thr Ser Trp Phe Ser Leu Pro Cys Val Met Thr Ala
    50                  55                  60

Val Tyr Leu Gly Gly Val Phe Gly Leu Thr Lys Tyr Phe Glu Gly Arg
65                  70                  75                  80

Lys Pro Met Gln Gly Leu Lys Asp Tyr Met Phe Thr Tyr Asn Leu Tyr
                85                  90                  95

Gln Val Ile Ile Asn Val Trp Cys Ile Ala Ala Phe Val Val Glu Val
            100                 105                 110

Arg Arg Ala Gly Met Ser Ala Val Gly Asn Lys Val Asp Leu Gly Pro
        115                 120                 125

Asn Ser Phe Arg Leu Gly Phe Val Thr Trp Val His Tyr Asn Asn Lys
    130                 135                 140

Tyr Val Glu Leu Leu Asp Thr Leu Trp Met Val Leu Arg Lys Lys Thr
145                 150                 155                 160

Gln Gln Val Ser Phe Leu His Val Tyr His His Val Leu Leu Ile Trp
                165                 170                 175

Ala Trp Phe Cys Val Val Lys Phe Cys Asn Gly Gly Asp Ala Tyr Phe
            180                 185                 190

Gly Gly Met Leu Asn Ser Ile Ile His Val Met Met Tyr Ser Tyr Tyr
        195                 200                 205

Thr Met Ala Leu Leu Gly Trp Ser Cys Pro Trp Lys Arg Tyr Leu Thr
    210                 215                 220

Gln Ala Gln Leu Val Gln Phe Cys Ile Cys Leu Ala His Ala Thr Trp
225                 230                 235                 240

Ala Ala Ala Thr Gly Val Tyr Pro Phe His Ile Cys Leu Val Glu Ile
                245                 250                 255

Trp Val Met Val Ser Met Leu Tyr Leu Phe Thr Lys Phe Tyr Asn Ser
                260                 265                 270

Ala Tyr Lys Gly Ala Ala Lys Gly Ala Ala Ala Ser Ser Asn Gly Ala
            275                 280                 285
```

```
Ala Ala Pro Ser Gly Ala Lys Pro Lys Ser Ile Lys Ala Asn
    290             295                 300
```

<210> SEQ ID NO 2
<211> LENGTH: 263
<212> TYPE: PRT
<213> ORGANISM: Isochrysis galbana

<400> SEQUENCE: 2

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Tyr Gln Asp Asn Leu Ala Thr Lys Lys Ser
                245                 250                 255

Ala Lys Ala Gly Lys Gln Leu
        260
```

<210> SEQ ID NO 3
<211> LENGTH: 263
<212> TYPE: PRT
<213> ORGANISM: Eutreptiella sp.

<400> SEQUENCE: 3

```
Met Ala Ala Val Ile Glu Val Ala Asn Glu Phe Ala Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
```

```
                      50                  55                  60
Phe Lys Trp Tyr Asn Leu Phe Met Ser Val Phe Ser Leu Val Ser Phe
 65                  70                  75                  80

Leu Cys Met Gly Tyr Ala Ile Tyr Thr Val Gly Leu Tyr Ser Asn Glu
                 85                  90                  95

Cys Asp Arg Ala Phe Asp Asn Ser Leu Phe Arg Phe Ala Thr Lys Val
             100                 105                 110

Phe Tyr Tyr Ser Lys Phe Leu Glu Tyr Ile Asp Ser Phe Tyr Leu Pro
             115                 120                 125

Leu Met Ala Lys Pro Leu Ser Phe Leu Gln Phe Phe His His Leu Gly
130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                 165                 170                 175

Tyr Tyr Trp Thr Arg Leu Met Lys Phe Asn Phe Pro Met Pro Lys Gln
             180                 185                 190

Leu Ile Thr Ala Met Gln Ile Thr Gln Phe Asn Val Gly Phe Tyr Leu
             195                 200                 205

Val Trp Trp Tyr Lys Asp Ile Pro Cys Tyr Arg Lys Asp Pro Met Arg
210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                 245                 250                 255

Thr Ala Asp Lys Lys Val Gln
             260

<210> SEQ ID NO 4
<211> LENGTH: 258
<212> TYPE: PRT
<213> ORGANISM: Euglena gracialis

<400> SEQUENCE: 4

Met Glu Val Val Asn Glu Ile Val Ser Ile Gly Gln Glu Val Leu Pro
  1               5                  10                  15

Lys Val Asp Tyr Ala Gln Leu Trp Ser Asp Ala Ser His Cys Glu Val
                 20                  25                  30

Leu Tyr Leu Ser Ile Ala Phe Val Ile Leu Lys Phe Thr Leu Gly Pro
             35                  40                  45

Leu Gly Pro Lys Gly Gln Ser Arg Met Lys Phe Val Phe Thr Asn Tyr
 50                  55                  60

Asn Leu Leu Met Ser Ile Tyr Ser Leu Gly Ser Phe Leu Ser Met Ala
 65                  70                  75                  80

Tyr Ala Met Tyr Thr Ile Gly Val Met Ser Asp Asn Cys Glu Lys Ala
                 85                  90                  95

Phe Asp Asn Asn Val Phe Arg Ile Thr Thr Gln Leu Phe Tyr Leu Ser
             100                 105                 110

Lys Phe Leu Glu Tyr Ile Asp Ser Phe Tyr Leu Pro Leu Met Gly Lys
             115                 120                 125

Pro Leu Thr Trp Leu Gln Phe Phe His His Leu Gly Ala Pro Met Asp
130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
```

```
                    165                 170                 175
Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
        210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 5
<211> LENGTH: 258
<212> TYPE: PRT
<213> ORGANISM: Euglena anabena

<400> SEQUENCE: 5

Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Gln Gly Lys
                245                 250                 255

Lys Glu

<210> SEQ ID NO 6
<211> LENGTH: 744
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tttcggtccg gattcccggg aattttttt cgtgttgcct ggctagtacg ccccctccc       60
tcctgtgacc ctccaccaca caccccccaa aggatggacg tcgcgactac gctggctggc     120
atcgcggcgg acgtgctgcc ccgcgtggac tacgcgcggc ttgggcgcga cgccgccgcc     180
tgcgaggttc tatacctttc gctgttcttc atcgccatga agttcatcct tcgcccctc      240
ggcgacaagg ggcaggcccg cctcaagtcg ctcttcaccc tctacaacct cgtgatgtcc     300
atctactccc tcggatcttt cgttgtaatg ggctacgcct tggcggatat cggagtgctc     360
ggtggtgatt gcgggaaagc attctcaaat cccatgttcc gcctcaccgc tcagttgttc     420
tacatcagca agtacgttga gtacatcgat tccttctacg tgcttctcac caacaagccc     480
ctgacctacc tgcagttctt ccaccacctc ggagccccg tcgacctctg gctcttcctg      540
cagtacgaaa acgaggcgct gtggatcttc gtcttcctca acggcttcat ccacttcatc     600
atgtacgggt actactgggc ccggctggtg aagctcccgt tccccgtgcc gaagtcgttc     660
atcacctcca tgcagatcat ccagttcaac ctgggcttct acctcgtgtg gcggtaccac     720
acaatcccgt gctaccgaca ggac                                            744

<210> SEQ ID NO 7
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Val Ala Thr Thr Leu Ala Gly Ile Ala Ala Asp Val Leu Pro
1               5                   10                  15
Arg Val Asp Tyr Ala Arg Leu Gly Arg Asp Ala Ala Ala Cys Glu Val
                20                  25                  30
Leu Tyr Leu Ser Leu Phe Phe Ile Ala Met Lys Phe Ile Leu Arg Pro
            35                  40                  45
Leu Gly Asp Lys Gly Gln Ala Arg Leu Lys Ser Leu Phe Thr Leu Tyr
        50                  55                  60
Asn Leu Val Met Ser Ile Tyr Ser Leu Gly Ser Phe Val Val Met Gly
65                  70                  75                  80
Tyr Ala Leu Ala Asp Ile Gly Val Leu Gly Gly Asp Cys Gly Lys Ala
                85                  90                  95
Phe Ser Asn Pro Met Phe Arg Leu Thr Ala Gln Leu Phe Tyr Ile Ser
            100                 105                 110
Lys Tyr Val Glu Tyr Ile Asp Ser Phe Tyr Val Leu Leu Thr Asn Lys
        115                 120                 125
Pro Leu Thr Tyr Leu Gln Phe Phe His His Leu Gly Ala Pro Val Asp
    130                 135                 140
Leu Trp Leu Phe Leu Gln Tyr Glu Asn Glu Ala Leu Trp Ile Phe Val
145                 150                 155                 160
Phe Leu Asn Gly Phe Ile His Phe Ile Met Tyr Gly Tyr Tyr Trp Ala
                165                 170                 175
Arg Leu Val Lys Leu Pro Phe Pro Val Pro Lys Ser Phe Ile Thr Ser
            180                 185                 190
```

Met Gln Ile Ile Gln Phe Asn Leu Gly Phe Tyr Leu Val Trp Arg Tyr
            195                 200                 205

His Thr Ile Pro Cys Tyr Arg Gln Asp
        210                 215

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (57)..(57)
<223> OTHER INFORMATION: a, c, g or t

<400> SEQUENCE: 8
aagcagtggt atcaacgcag agtactttt tttttttttt tttttttttt tttttvn        57

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggcgctgtg gatcttcgtc ttcc                                            24

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctaatacgac tcactatagc aagcagtggt atcaacgcag agt                        43

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctaatacgac tcactatagg gc                                               22

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccccgtgcc gaagtcgttc atcacc                                           26

<210> SEQ ID NO 13
<211> LENGTH: 548
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 13
tccccgtgcc gaagtcgttc atcacctcca tgcagatcat ccagttcaac ctgggcttct     60
acctcgtgtg gcggtaccac actatcccgt gctaccgaca ggacccaatg cgaatgttcg    120
cttggctctt caactacttc tacgtgggag tggtcttact gctgttttg aatttctacg     180 tgcacacgta cgtgatcaag aaggcgcggc ggctggcgaa ggatgagaag aaagtggact    240
agcggagccg gcggcgccca ctgggacccg gtggctccgt gcgcccttcc tcgcccggca    300
tcgaacccac ccaytccccc actagcctcc acgatactcc cttccctcct ccccagtcca    360
ccgtcgaaag gtatccaggc ccttcgactc acacttgcga ccagatggcg gtttaacctc    420
tgcgcgactc ggagagttgc cctaaccatc tgttctagaa ctcgcgattg gactgtgttg    480
aactggatcc gatgaccctc gttttccat accgttgtwm aaaaaaaaaa aaaaaaaaa     540 aaaaaaaa                                                             548

<210> SEQ ID NO 14
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Val Pro Lys Ser Phe Ile Thr Ser Met Gln Ile Ile Gln Phe Asn
1               5                   10                  15

Leu Gly Phe Tyr Leu Val Trp Arg Tyr His Thr Ile Pro Cys Tyr Arg
            20                  25                  30

Gln Asp Pro Met Arg Met Phe Ala Trp Leu Phe Asn Tyr Phe Tyr Val
        35                  40                  45

Gly Val Val Leu Leu Leu Phe Leu Asn Phe Tyr Val His Thr Tyr Val
    50                  55                  60

Ile Lys Lys Ala Arg Arg Leu Ala Lys Asp Glu Lys Lys Val Asp
65                  70                  75

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccatggat ccatggacgt cgcgactacg ctgg                                34

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgcgtaagc ttctagtcca ctttcttctc atccttc                             37
```

<210> SEQ ID NO 17
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atggacgtcg cgactacgct ggctggcatc gcggcggacg tgctgccccg cgtggactac    60
gcgcggcttg ggcgcgacgc cgccgcctgc gaggttctat acctttcgct gttcttcatc   120
gccatgaagt tcatccttcg cccctcggc gacaaggggc aggcccgcct caagtcgctc    180
ttcaccctct acaacctcgt gatgtccatc tactccctcg gatctttcgt tgtaatgggc   240
tacgccttgg cggatatcgg agtgctcggt ggtgattgcg ggaaagcatt ctcaaatccc   300
atgttccgcc tcaccgctca gttgttctac atcagcaagt acgttgagta catcgattcc   360
ttctacgtgc ttctccaccaa caagcccctg acctacctgc agttcttcca ccacctcgga   420
gcccccgtcg acctctggct cttcctgcag tacgaaaacg aggcgctgtg gatcttcgtc   480
ttcctcaacg gcttcatcca cttcatcatg tacgggtact actgggcccg gctggtgaag   540
ctcccgttcc ccgtgccgaa gtcgttcatc acctccatgc agatcatcca gttcaacctg   600
ggcttctacc tcgtgtggcg gtaccacaca atcccgtgct accgacagga cccaatgcga   660
atgttcgctt ggctcttcaa ctacttctac gtgggagtgg tcttactgct gttttttgaat   720 ttctacgtgc acacgtacgt gatcaagaaa gcgcggcggc tggcgaagga tgagaagaaa   780
gtggactag                                                            789
```

<210> SEQ ID NO 18
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Val Ala Thr Thr Leu Ala Gly Ile Ala Ala Asp Val Leu Pro
1               5                   10                  15

Arg Val Asp Tyr Ala Arg Leu Gly Arg Asp Ala Ala Ala Cys Glu Val
            20                  25                  30

Leu Tyr Leu Ser Leu Phe Phe Ile Ala Met Lys Phe Ile Leu Arg Pro
        35                  40                  45

Leu Gly Asp Lys Gly Gln Ala Arg Leu Lys Ser Leu Phe Thr Leu Tyr
    50                  55                  60

Asn Leu Val Met Ser Ile Tyr Ser Leu Gly Ser Phe Val Val Met Gly
65                  70                  75                  80

Tyr Ala Leu Ala Asp Ile Gly Val Leu Gly Gly Asp Cys Gly Lys Ala
                85                  90                  95

Phe Ser Asn Pro Met Phe Arg Leu Thr Ala Gln Leu Phe Tyr Ile Ser
            100                 105                 110

Lys Tyr Val Glu Tyr Ile Asp Ser Phe Tyr Val Leu Thr Asn Lys
        115                 120                 125

Pro Leu Thr Tyr Leu Gln Phe Phe His His Leu Gly Ala Pro Val Asp
    130                 135                 140

Leu Trp Leu Phe Leu Gln Tyr Glu Asn Glu Ala Leu Trp Ile Phe Val
145                 150                 155                 160

Phe Leu Asn Gly Phe Ile His Phe Ile Met Tyr Gly Tyr Tyr Trp Ala

```
                    165                 170                 175
Arg Leu Val Lys Leu Pro Phe Pro Val Pro Lys Ser Phe Ile Thr Ser
                180                 185                 190

Met Gln Ile Ile Gln Phe Asn Leu Gly Phe Tyr Leu Val Trp Arg Tyr
            195                 200                 205

His Thr Ile Pro Cys Tyr Arg Gln Asp Pro Met Arg Met Phe Ala Trp
        210                 215                 220

Leu Phe Asn Tyr Phe Tyr Val Gly Val Val Leu Leu Leu Phe Leu Asn
225                 230                 235                 240

Phe Tyr Val His Thr Tyr Val Ile Lys Lys Ala Arg Arg Leu Ala Lys
                245                 250                 255

Asp Glu Lys Lys Val Asp
            260
```

<210> SEQ ID NO 19
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggacgtcg cgactacgct ggccggcatc gcggcggacg tgctgccccg cgtggactac      60
gcgcggcttg gcgcgacgc cgtcgcctgc gaggttctat acctttcgct gttcttcatc     120
gccatgaagt tcatccttcg cccctcggc gacaagggc aggcccgcct caagtcgctc      180
ttcaccctct acaacctcgt gatgtccatc tactccctcg atctttcgt tataatgggc     240
tacgccttgg cggatatcgg agtgctcggt ggtgattgcg ggaaagcatt ctcaaatccc    300
ttgttccgca tcaccgctca gttgttctac atcagcaagt acgttgagta catcgattcc    360
ttctacgtgc ttctcaccaa caagcccctg acctacctgc agttcttcca ccacctcgga    420
gcccccgtcg acctctggct cttcctgcag tacgaaaacg aggcgctgtg gatcttcgtc    480
ttcctcaacg gcttcatcca cttcatcatg tacgggtact actgggcccg gctggtgaag    540
ctcccgttcc ccgtgccgaa gtcgttcatc acctccatgc agatcatcca gttcaacctg    600
ggcttctacc tcgtgtggcg gtaccacact atcccgtgct accgacagga cccaatgcga    660
atgttcgctt ggctcttcaa ctacttctac gtgggagtgg tcttactgct gtttttgaat    720
ttctacgtgc acacgtacgt gatcaagaag gcgcggcggc tggcgaagga tgagaagaaa    780
gtggactag                                                            789
```

<210> SEQ ID NO 20
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Asp Val Ala Thr Thr Leu Ala Gly Ile Ala Ala Asp Val Leu Pro
1               5                   10                  15

Arg Val Asp Tyr Ala Arg Leu Gly Arg Asp Ala Val Ala Cys Glu Val
            20                  25                  30

Leu Tyr Leu Ser Leu Phe Phe Ile Ala Met Lys Phe Ile Leu Arg Pro
        35                  40                  45

Leu Gly Asp Lys Gly Gln Ala Arg Leu Lys Ser Leu Phe Thr Leu Tyr
```

```
                50                  55                  60
Asn Leu Val Met Ser Ile Tyr Ser Leu Gly Ser Phe Val Ile Met Gly
 65                  70                  75                  80

Tyr Ala Leu Ala Asp Ile Gly Val Leu Gly Gly Asp Cys Gly Lys Ala
                 85                  90                  95

Phe Ser Asn Pro Leu Phe Arg Ile Thr Ala Gln Leu Phe Tyr Ile Ser
                100                 105                 110

Lys Tyr Val Glu Tyr Ile Asp Ser Phe Tyr Val Leu Thr Asn Lys
                115                 120                 125

Pro Leu Thr Tyr Leu Gln Phe Phe His His Leu Gly Ala Pro Val Asp
                130                 135                 140

Leu Trp Leu Phe Leu Gln Tyr Glu Asn Glu Ala Leu Trp Ile Phe Val
145                 150                 155                 160

Phe Leu Asn Gly Phe Ile His Phe Ile Met Tyr Gly Tyr Tyr Trp Ala
                165                 170                 175

Arg Leu Val Lys Leu Pro Phe Pro Val Pro Lys Ser Phe Ile Thr Ser
                180                 185                 190

Met Gln Ile Ile Gln Phe Asn Leu Gly Phe Tyr Leu Val Trp Arg Tyr
                195                 200                 205

His Thr Ile Pro Cys Tyr Arg Gln Asp Pro Met Arg Met Phe Ala Trp
                210                 215                 220

Leu Phe Asn Tyr Phe Tyr Val Gly Val Val Leu Leu Phe Leu Asn
225                 230                 235                 240

Phe Tyr Val His Thr Tyr Val Ile Lys Lys Ala Arg Arg Leu Ala Lys
                245                 250                 255

Asp Glu Lys Lys Val Asp
                260

<210> SEQ ID NO 21
<211> LENGTH: 312
<212> TYPE: PRT
<213> ORGANISM: Mus musculus

<400> SEQUENCE: 21

Met Gly Leu Leu Asp Ser Glu Pro Gly Ser Val Leu Asn Ala Met Ser
 1               5                  10                  15

Thr Ala Phe Asn Asp Thr Val Glu Phe Tyr Arg Trp Thr Trp Thr Ile
                 20                  25                  30

Ala Asp Lys Arg Val Ala Asp Trp Pro Leu Met Gln Ser Pro Trp Pro
                 35                  40                  45

Thr Ile Ser Ile Ser Thr Leu Tyr Leu Leu Phe Val Trp Leu Gly Pro
 50                  55                  60

Lys Trp Met Lys Asp Arg Glu Pro Phe Gln Met Arg Leu Val Leu Ile
 65                  70                  75                  80

Ile Tyr Asn Phe Gly Met Val Leu Leu Asn Leu Phe Ile Phe Arg Glu
                 85                  90                  95

Leu Phe Met Gly Ser Tyr Asn Ala Gly Tyr Ser Tyr Ile Cys Gln Ser
                100                 105                 110

Val Asp Tyr Ser Asn Asp Val Asn Glu Val Arg Ile Ala Ala Ala Leu
                115                 120                 125

Trp Trp Tyr Phe Val Ser Lys Gly Val Glu Tyr Leu Asp Thr Val Phe
                130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
```

```
                    165                 170                 175
Ala Gly Gly Gln Ala Phe Phe Gly Ala Gln Met Asn Ser Phe Ile His
            180                 185                 190
Val Ile Met Tyr Ser Tyr Tyr Gly Leu Thr Ala Phe Gly Pro Trp Ile
        195                 200                 205
Gln Lys Tyr Leu Trp Trp Lys Arg Tyr Leu Thr Met Leu Gln Leu Val
    210                 215                 220
Gln Phe His Val Thr Ile Gly His Thr Ala Leu Ser Leu Tyr Thr Asp
225                 230                 235                 240
Cys Pro Phe Pro Lys Trp Met His Trp Ala Leu Ile Ala Tyr Ala Ile
                245                 250                 255
Ser Phe Ile Phe Leu Phe Leu Asn Phe Tyr Thr Arg Thr Tyr Asn Glu
            260                 265                 270
Pro Lys Gln Ser Lys Thr Gly Lys Thr Ala Thr Asn Gly Ile Ser Ser
        275                 280                 285
Asn Gly Val Asn Lys Ser Glu Lys Ala Leu Glu Asn Gly Lys Pro Gln
    290                 295                 300
Lys Asn Gly Lys Pro Lys Gly Glu
305                 310

<210> SEQ ID NO 22
<211> LENGTH: 296
<212> TYPE: PRT
<213> ORGANISM: Homo sapiens

<400> SEQUENCE: 22

Met Glu His Leu Lys Ala Phe Asp Asp Glu Ile Asn Ala Phe Leu Asp
1               5                   10                  15
Asn Met Phe Gly Pro Arg Asp Ser Arg Val Arg Gly Trp Phe Met Leu
            20                  25                  30
Asp Ser Tyr Leu Pro Thr Phe Phe Leu Thr Val Met Tyr Leu Leu Ser
        35                  40                  45
Ile Trp Leu Gly Asn Lys Tyr Met Lys Asn Arg Pro Ala Leu Ser Leu
    50                  55                  60
Arg Gly Ile Leu Thr Leu Tyr Asn Leu Gly Ile Thr Leu Leu Ser Ala
65                  70                  75                  80
Tyr Met Leu Ala Glu Leu Ile Leu Ser Thr Trp Glu Gly Gly Tyr Asn
                85                  90                  95
Leu Gln Cys Gln Asp Leu Thr Ser Ala Gly Glu Ala Asp Ile Arg Val
            100                 105                 110
Ala Lys Val Leu Trp Trp Tyr Tyr Phe Ser Lys Ser Val Glu Phe Leu
        115                 120                 125
Asp Thr Ile Phe Phe Val Leu Arg Lys Lys Thr Ser Gln Ile Thr Phe
    130                 135                 140
Leu His Val Tyr His His Ala Ser Met Phe Asn Ile Trp Trp Cys Val
145                 150                 155                 160
Leu Asn Trp Ile Pro Cys Gly Gln Ser Phe Phe Gly Pro Thr Leu Asn
                165                 170                 175
Ser Phe Ile His Ile Leu Met Tyr Ser Tyr Tyr Gly Leu Ser Val Phe
            180                 185                 190
Pro Ser Met His Lys Tyr Leu Trp Trp Lys Lys Tyr Leu Thr Gln Ala
        195                 200                 205
Gln Leu Val Gln Phe Val Leu Thr Ile Thr His Thr Met Ser Ala Val
    210                 215                 220
Val Lys Pro Cys Gly Phe Pro Phe Gly Cys Leu Ile Phe Gln Ser Ser
```

```
                    225                 230                 235                 240
Tyr Met Leu Thr Leu Val Ile Leu Phe Leu Asn Phe Tyr Val Gln Thr
                245                 250                 255
Tyr Arg Lys Lys Pro Met Lys Lys Asp Met Gln Glu Pro Pro Ala Gly
            260                 265                 270
Lys Glu Val Lys Asn Gly Phe Ser Lys Ala Tyr Phe Thr Ala Ala Asn
        275                 280                 285
Gly Val Met Asn Lys Lys Ala Gln
    290                 295
```

<210> SEQ ID NO 23
<211> LENGTH: 288
<212> TYPE: PRT
<213> ORGANISM: Caenorhabditis elegans

<400> SEQUENCE: 23

```
Met Ala Gln His Pro Leu Val Gln Arg Leu Leu Asp Val Lys Phe Asp
1               5                   10                  15
Thr Lys Arg Phe Val Ala Ile Ala Thr His Gly Pro Lys Asn Phe Pro
            20                  25                  30
Asp Ala Glu Gly Arg Lys Phe Phe Ala Asp His Phe Asp Val Thr Ile
        35                  40                  45
Gln Ala Ser Ile Leu Tyr Met Val Val Phe Gly Thr Lys Trp Phe
    50                  55                  60
Met Arg Asn Arg Gln Pro Phe Gln Leu Thr Ile Pro Leu Asn Ile Trp
65                  70                  75                  80
Asn Phe Ile Leu Ala Ala Phe Ser Ile Ala Gly Ala Val Lys Met Thr
                85                  90                  95
Pro Glu Phe Phe Gly Thr Ile Ala Asn Lys Gly Ile Val Ala Ser Tyr
            100                 105                 110
Cys Lys Val Phe Asp Phe Thr Lys Gly Glu Asn Gly Tyr Trp Val Trp
        115                 120                 125
Leu Phe Met Ala Ser Lys Leu Phe Glu Leu Val Asp Thr Ile Phe Leu
    130                 135                 140
Val Leu Arg Lys Arg Pro Leu Met Phe Leu His Trp Tyr His Ile
145                 150                 155                 160
Leu Thr Met Ile Tyr Ala Trp Tyr Ser His Pro Leu Thr Pro Gly Phe
                165                 170                 175
Asn Arg Tyr Gly Ile Tyr Leu Asn Phe Val His Ala Phe Met Tyr
            180                 185                 190
Ser Tyr Tyr Phe Leu Arg Ser Met Lys Ile Arg Val Pro Gly Phe Ile
        195                 200                 205
Ala Gln Ala Ile Thr Ser Leu Gln Ile Val Gln Phe Ile Ile Ser Cys
    210                 215                 220
Ala Val Leu Ala His Leu Gly Tyr Leu Met His Phe Thr Asn Ala Asn
225                 230                 235                 240
Cys Asp Phe Glu Pro Ser Val Phe Lys Leu Ala Val Phe Met Asp Thr
                245                 250                 255
Thr Tyr Leu Ala Leu Phe Val Asn Phe Phe Leu Gln Ser Tyr Val Leu
            260                 265                 270
Arg Gly Gly Lys Asp Lys Tyr Lys Ala Val Pro Lys Lys Asn Asn
        275                 280                 285
```

<210> SEQ ID NO 24
<211> LENGTH: 33
<212> TYPE: DNA

<213> ORGANISM: Artificial Sequence
<220> FEATURE:
<223> OTHER INFORMATION: Description of Artificial Sequence: Synthetic primer

<400> SEQUENCE: 24
tatagaattc aaatggacgt cgcgactacg ctg         33

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tattctcgag ttctagtcca ctttcttctc atccttc         37

<210> SEQ ID NO 26
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26
ggatccatgg acgtcgcgac tacgctggct ggcatcgcgg cggacgtgct gccccgcgtg      60
gactacgcgc ggcttgggcg cgacgccgcc gcctgcgagg ttctatacct ttcgctgttc     120
ttcatcgcca tgaagttcat ccttcgcccc ctcggcgaca aggggcaggc ccgcctcaag     180
tcgctcttca ccctctacaa cctcgtgatg tccatctact ccctcggatc tttcgttgta     240
atgggctacg ccttggcgga tatcggagtg ctcggtggtg attgcgggaa agcattctca     300
aatcccatgt ccgcctcac cgctcagttg ttctacatca gcaagtacgt tgagtacatc      360
gattccttct acgtgcttct caccaacaag ccctgacct acctgcagtt cttccaccac      420
ctcggagccc ccgtcgacct ctggctcttc ctgcagtacg aaaacgaggc gctgtggatc     480
ttcgtcttcc tcaacggctt catccacttc atcatgtacg ggtactactg ggcccggctg     540
gtgaagctcc cgttcccgt gccgaagtcg ttcatcacct ccatgcagat catccagttc     600
aacctgggct tctacctcgt gtggcggtac cacacaatcc cgtgctaccg acaggaccca     660
atgcgaatgt tcgcttggct cttcaactac ttctacgtgg gagtggtctt actgctgttt     720
ttgaatttct acgtgcacac gtacgtgatc aagaaagcgc ggcggctggc gaaggatgag     780
aagaaagtgg actagaagct t                                                801

<210> SEQ ID NO 27
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
ggatccatgg acgtcgcgac tacgctggcc ggcatcgcgg cggacgtgct gccccgcgtg      60
gactacgcgc ggcttgggcg cgacgccgtc gcctgcgagg ttctatacct ttcgctgttc     120
ttcatcgcca tgaagttcat ccttcgcccc ctcggcgaca aggggcaggc ccgcctcaag     180
tcgctcttca ccctctacaa cctcgtgatg tccatctact ccctcggatc tttcgttata     240

-continued

```
atgggctacg ccttggcgga tatcggagtg ctcggtggtg attgcgggaa agcattctca    300
aatcccttgt tccgcatcac cgctcagttg ttctacatca gcaagtacgt tgagtacatc    360
gattccttct acgtgcttct caccaacaag cccctgacct acctgcagtt cttccaccac    420
ctcggagccc ccgtcgacct ctggctcttc ctgcagtacg aaaacgaggc gctgtggatc    480
ttcgtcttcc tcaacggctt catccacttc atcatgtacg ggtactactg ggcccggctg    540
gtgaagctcc cgttccccgt gccgaagtcg ttcatcacct ccatgcagat catccagttc    600
aacctgggct tctacctcgt gtggcggtac cacactatcc cgtgctaccg acaggaccca    660
atgcgaatgt tcgcttggct cttcaactac ttctacgtgg gagtggtctt actgctgttt    720
ttgaatttct acgtgcacac gtacgtgatc aagaaggcgc ggcggctggc gaaggatgag    780
aagaaagtgg actagaagct t                                              801
```

```
<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 28

His Xaa Xaa His His
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 29

Gln Xaa Xaa His His
1               5

<210> SEQ ID NO 30
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Arg Ser Arg Arg Arg Pro Leu Gly Pro Gly Gly Ser Val Arg Pro Ser
1               5                   10                  15

Ser Pro Gly Ile Glu Pro Thr His Ser Pro Thr Ser Leu His Asp Thr
                20                  25                  30

Pro Phe Pro Pro Pro Gln Ser Thr Val Glu Arg Tyr Pro Gly Pro Ser
            35                  40                  45

Thr His Thr Cys Asp Gln Met Ala Val
        50                  55
```

```
<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Leu Arg Asp Ser Glu Ser Cys Pro Asn His Leu Phe
1               5                  10

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Any amino acid

<400> SEQUENCE: 32

Asn Ser Arg Leu Asp Cys Val Glu Leu Asp Pro Met Thr Leu Val Phe
1               5                   10                  15

Pro Tyr Arg Cys Xaa Lys Lys Lys Lys Lys Lys Lys Lys Lys
            20                  25                  30
```